US010961588B2

(12) United States Patent
Herault

(10) Patent No.: US 10,961,588 B2
(45) Date of Patent: Mar. 30, 2021

(54) HEMOPATHY PROGNOSIS METHOD

(71) Applicants: Centre National De La Recherche Scientifique (CNRS), Paris (FR); Université de Tours, Tours (FR)

(72) Inventor: Olivier Herault, La Tremblaye (FR)

(73) Assignee: UNIVERSITÉ DE TOURS, Tours (FR)

( * ) Notice: Subject to any disclaimer, the term of this patent is extended or adjusted under 35 U.S.C. 154(b) by 975 days.

(21) Appl. No.: 15/531,242

(22) PCT Filed: Nov. 26, 2015

(86) PCT No.: PCT/FR2015/053218
§ 371 (c)(1),
(2) Date: May 26, 2017

(87) PCT Pub. No.: WO2016/083742
PCT Pub. Date: Jun. 2, 2016

(65) Prior Publication Data
US 2017/0327896 A1    Nov. 16, 2017

(30) Foreign Application Priority Data

Nov. 27, 2014 (FR) ...................................... 1461553

(51) Int. Cl.
*C12Q 1/6886* (2018.01)
*G16B 25/10* (2019.01)

(52) U.S. Cl.
CPC .......... *C12Q 1/6886* (2013.01); *G16B 25/10* (2019.02); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

2007/0154931 A1    7/2007    Radich et al.

FOREIGN PATENT DOCUMENTS

| WO | 2005118851 A1 | 12/2005 |
| WO | 2012049329 A1 | 4/2012 |
| WO | 2012085188 A1 | 6/2012 |

OTHER PUBLICATIONS

Tanaka et al. Expression pattern of oxidative stress and antioxidant defense-related genes in the aging Fischer 344/NHsd rat cochlea Neurobiology of Aging vol. 33, pp. 1842.e1-1842.e14 and supplemental information (Year: 2012).*

Olivier Herault, et al., A role for GPx3 in activity of normal and leukemia stem cells, The Rockefeller University Press, J. Exp. Med., vol. 203, No. 5, pp. 895-901, download from jem.rupress.org on Jul. 21, 2015.

Anonymous, RT2 Prtiler PCR Array: Human Oxidative Stress and Antioxidant Defense, Product Specification Sheet, www.SABiosciences.com, pp. 1-4.

Rizwan Ahmad, et al., Oxidative Stress and Antioxidant Status in Patients With Chronic Myeloid Leukemia, Indian Journal of Clinical Biochemistry, 2008, vol. 23, No. 4, Department of Biochemistry and Medicine, pp. 328-333, C.S.M. Medical University, Lucknow, India.

Wensheng Yan, et al., GPX2, a Direct Target of p63, Inhibits Oxidative Stress-induced Apoptosis in a p53-dependent Manner, Journal of Biological Chemistry, vol. 281, No. 12, Mar. 24, 2006, pp. 7856-7862, USA.

Chiara Gorrini, et al., Modulation of oxidative stress as an anticancer strategy, Nature Reviews/Drug Discovery, 2013, vol. 12, pp. 931-947.

Michele Baccarani, et al., European LeukemiaNet recommendations for the management of chronic myeloid leukemia: 2013, Blood, Aug. 8, 2013, vol. 122, No. 6, The American Society of Hematology, pp. 872-884.

International Search Report pertaining to PCT/FR2015/053218, filed Nov. 26, 2015, 4 pages.

Written Opinion pertaining to PCT/FR2015/053218, filed Nov. 26, 2015, 7 pages.

* cited by examiner

*Primary Examiner* — John S Brusca
(74) *Attorney, Agent, or Firm* — Dinsmore & Shohl LLP

(57) ABSTRACT

This invention relates to an in vitro method for prognosis of the response to a chemotherapy of an individual suffering from chronic myeloid leukemia, comprising a. a step of measuring the expression level of at least one subgroup of genes chosen from a group of genes, b. a comparing step, and c. a step of determining a score S such that—if S is less than 1, said individual will have more than a 40% chance of responding to the chemotherapy, and—if S is greater than or equal to 1, said individual will have less than a 40% chance of responding to the chemotherapy.

12 Claims, 3 Drawing Sheets

Specification includes a Sequence Listing.

SEQUENCE LISTING

<160> NUMBER OF SEQ ID NOS: 47

<210> SEQ ID NO 1
<211> LENGTH: 2300
<212> TYPE: DNA
<213> ORGANISM: Homo sapiens

<400> SEQUENCE: 1

```
actcggggca acaggcagat ttgcctgctg agggtggaga cccacgagcc gaggcctcct      60
gcagtgttct gcacagcaaa ccgcacgcta tggctgacag ccgggatccc gccagcgacc     120
agatgcagca ctggaaggag cagcgggccg cgcagaaagc tgatgtcctg accactggag     180
ctggtaaccc agtaggagac aaacttaatg ttattacagt agggccccgt gggcccttc      240
ttgttcagga tgtggttttc actgatgaaa tggctcattt tgaccgagag agaattcctg     300
agagagttgt gcatgctaaa ggagcagggg cctttggcta ctttgaggtc acacatgaca     360
ttaccaaata ctccaaggca aaggtatttg agcatattgg aaagaagact cccatcgcag     420
ttcggttctc cactgttgct ggagaatcgg gttcagctga cacagttcgg gaccctcgtg     480
ggtttgcagt gaaattttac acagaagatg gtaactggga tctcgttgga aataacaccc     540
ccatttttctt catcagggat cccatattgt ttccatcttt tatccacagc caaaagagaa     600
atcctcagac acatctgaag gatccggaca tggtctggga cttctggagc ctacgtcctg     660
agtctctgca tcaggtttct ttcttgttca gtgatcgggg gattccagat ggacatcgcc     720
acatgaatgg atatggatca catactttca agctggttaa tgcaaatggg gaggcagttt     780
attgcaaatt ccattataag actgaccagg gcatcaaaaa cctttctgtt gaagatgcgg     840
cgagactttc ccaggaagat cctgactatg gcatccggga tctttttaac gccattgcca     900
caggaaagta cccctcctgg actttttaca tccaggtcat gacatttaat caggcagaaa     960
cttttccatt taatccattc gatctcacca aggtttggcc tcacaaggac tacctctca    1020
tcccagttgg taaactggtc ttaaaccgga atccagttaa ttactttgct gaggttgaac    1080
agatagcctt cgacccaagc aacatgccac ctggcattga ggccagtcct gacaaaatgc    1140
ttcagggccg ccttttttgcc tatcctgaca ctcaccgcca tcgcctggga cccaattatc    1200
ttcatatacc tgtgaactgt ccctaccgtg ctcgagtggc caactaccag cgtgacggcc    1260
cgatgtgcat gcaggacaat cagggtggtg ctccaaatta ctaccccaac agctttggtg    1320
ctccggaaca acagccttct gccctggagc acagcatcca atattctgga gaagtgcgga    1380
gattcaacac tgccaatgat gataacgtta ctcaggtgcg ggcattctat gtgaacgtgc    1440
tgaatgagga acagaggaaa cgtctgtgtg agaacattgc cggccacctg aaggatgcac    1500
aaatttttcat ccagaagaaa gcggtcaaga acttcactga ggtccaccct gactacggga    1560
gccacatcca ggctcttctg gacaagtaca atgctgagaa gcctaagaat gcgattcaca    1620
cctttgtgca gtccggatct cacttggcgg caagggagaa ggcaaatctg tgaggccggg    1680
gccctgcacc tgtgcagcga agcttagcgt tcatccgtgt aacccgctca tcactggatg    1740
aagattctcc tgtgctagat gtgcaaatgc aagctagtgg cttcaaaata gagaatccca    1800
```

| | |
|---|---|
| ctttctatag cagattgtgt aacaatttta atgctatttc cccagggaa aatgaaggtt | 1860 |
| aggatttaac agtcatttaa aaaaaaaatt tgttttgacg gatgattgga ttattcattt | 1920 |
| aaaatgatta gaaggcaagt tctagctag aaatatgatt ttatttgaca aaatttgttg | 1980 |
| aaattatgta tgtttacata tcacctcatg gcctattata ttaaaatatg gctataaata | 2040 |
| tataaaaaga aagataaag atgatctact cagaaatttt tattttttcta aggttctcat | 2100 |
| aggaaaagta catttaatac agcagtgtca tcagaagata acttgagcac cgtcatggct | 2160 |
| taatgtttat tcctgataat aattgatcaa attcattttt ttcactggag ttacattaat | 2220 |
| gttaattcag cactgatttc acaacagatc aatttgtaat tgcttacatt tttacaataa | 2280 |
| ataatctgta cgtaagaaca | 2300 |

<210> SEQ ID NO 2
<211> LENGTH: 981
<212> TYPE: DNA
<213> ORGANISM: Homo sapiens

<400> SEQUENCE: 2

| | |
|---|---|
| gtttggggcc agagtgggcg aggcgcggag gtctggccta taaagtagtc gcggagacgg | 60 |
| ggtgctggtt tgcgtcgtag tctcctgcag cgtctggggt ttccgttgca gtcctcggaa | 120 |
| ccaggacctc ggcgtggcct agcgagttat ggcgacgaag gccgtgtgcg tgctgaaggg | 180 |
| cgacggccca gtgcagggca tcatcaattt cgagcagaag gaaagtaatg gaccagtgaa | 240 |
| ggtgtgggga agcattaaag gactgactga aggcctgcat ggattccatg ttcatgagtt | 300 |
| tggagataat acagcaggct gtaccagtgc aggtcctcac tttaatcctc tatccagaaa | 360 |
| acacggtggg ccaaaggatg aagagaggca tgttggagac ttgggcaatg tgactgctga | 420 |
| caaagatggt gtggccgatg tgtctattga agattctgtg atctcactct caggagacca | 480 |
| ttgcatcatt ggccgcacac tggtggtcca tgaaaaagca gatgacttgg gcaaaggtgg | 540 |
| aaatgaagaa agtacaaaga caggaaacgc tggaagtcgt ttggcttgtg tgtaattgg | 600 |
| gatcgcccaa taaacattcc cttggatgta gtctgaggcc ccttaactca tctgttatcc | 660 |
| tgctagctgt agaaatgtat cctgataaac attaaacact gtaatcttaa aagtgtaatt | 720 |
| gtgtgacttt ttcagagttg cttttaaagta cctgtagtga gaaactgatt tatgatcact | 780 |
| tggaagattt gtatagtttt ataaaactca gttaaaatgt ctgtttcaat gacctgtatt | 840 |
| ttgccagact taaatcacag atgggtatta aacttgtcag aatttctttg tcattcaagc | 900 |
| ctgtgaataa aaaccctgta tggcacttat tatgaggcta ttaaaagaat ccaaattcaa | 960 |
| actaaaaaaa aaaaaaaaa a | 981 |

<210> SEQ ID NO 3
<211> LENGTH: 921
<212> TYPE: DNA
<213> ORGANISM: Homo sapiens

<400> SEQUENCE: 3

| | |
|---|---|
| cagttaaaag gaggcgcctg ctggcctccc cttacagtgc ttgttcgggg cgctccgctg | 60 |
| gcttcttgga caattgcgcc atgtgtgctg ctcggctagc ggcggcggcg gcggcggccc | 120 |
| agtcggtgta tgccttctcg gcgcgcccgc tggccggcgg ggagcctgtg agcctgggct | 180 |
| ccctgcgggg caaggtacta cttatcgaga atgtggcgtc cctctgaggc accacggtcc | 240 |
| gggactacac ccagatgaac gagctgcagc ggcgcctcgg accccggggc ctggtggtgc | 300 |
| tcggcttccc gtgcaaccag tttgggcatc aggagaacgc caagaacgaa gagattctga | 360 |

```
attccctcaa gtacgtccgg cctggtggtg ggttcgagcc caacttcatg ctcttcgaga      420
agtgcgaggt gaacggtgcg ggggcgcacc ctctcttcgc cttcctgcgg gaggccctgc      480
cagctcccag cgacgacgcc accgcgctta tgaccgaccc caagctcatc acctggtctc      540
cggtgtgtcg caacgatgtt gcctggaact ttgagaagtt cctggtgggc cctgacggtg      600
tgcccctacg caggtacagc cgccgcttcc agaccattga catcgagcct gacatcgaag      660
ccctgctgtc tcaagggccc agctgtgcct agggcgcccc tcctaccccg gctgcttggc      720
agttgcagtg ctgctgtctc ggggggtttt tcatctatga gggtgtttcc tctaaaccta      780
cgagggagga acacctgatc ttacagaaaa taccacctcg agatgggtgc tggtcctgtt      840
gatcccagtc tctgccagac caaggcgagt tccccacta ataaagtgcc gggtgtcagc      900
agaaaaaaaa aaaaaaaaaa a                                                921

<210> SEQ ID NO 4
<211> LENGTH: 942
<212> TYPE: DNA
<213> ORGANISM: Homo sapiens

<400> SEQUENCE: 4
gagcgctctg gagggcgtgg ccgtgggaaa ggaggcgcgg aaagccgacg cgcgtccatt       60
ggtcggctgg acgaggggag gagccgctgg ctcccagccc cgccgcgatg agcctcggcc      120
gcctttgccg cctactgaag ccggcgctgc tctgtggggc tctggccgcg cctggcctgg      180 ccggaccat gtgcgcgtcc cggacgact ggcgctgtgc gcgctccatg cacgagtttt       240
ccgccaagga catcgacggg cacatggtta acctggacaa gtaccggggc ttcgtgtgca      300
tcgtcaccaa cgtggcctcc cagtgaggca agaccgaagt aaactacact cagctcgtcg      360
acctgcacgc ccgatacgct gagtgtggtt tgcggatcct ggccttcccg tgtaaccagt      420
tcgggaagca ggagccaggg agtaacgaag agatcaaaga gttcgccgcg ggctacaacg      480
tcaaattcga tatgttcagc aagatctgcg tgaacgggga cgacgcccac ccgctgtgga      540
agtggatgaa gatccaaccc aagggcaagg gcatcctggg aaatgccatc aagtggaact      600
tcaccaagtt cctcatcgac aagaacggct gcgtggtgaa gcgctacgga cccatggagg      660
agcccctggt gatagagaag gacctgcccc actatttcta gctccacaag tgtgtggccc      720
cgcccgagcc cctgcccacg cccttggagc cttccaccgg cactcatgac ggcctgcctg      780
caaacctgct ggtggggcag acccgaaaat ccagcgtgca ccccgccgga ggaaggtccc      840
atggcctgct gggcttggct cggcgccccc acccctggct accttgtggg aataaacaga      900
caaattagcc tgctggaaaa aaaaaaaaaa aaaaaaaaa aa                          942

<210> SEQ ID NO 5
<211> LENGTH: 1262
<212> TYPE: DNA
<213> ORGANISM: Homo sapiens

<400> SEQUENCE: 5
actctcgcga gatccctact ggctataaag gcagcgcccc ggagagctct tgcgcgtctt       60
gttcttgcct ggtgtcggtg gttagtttct gcgacttgtg ttgggactgg tgagtgtggg      120
cagtgcggcc cctgcggagt gaggcgcggc gcgcccttct tgcctgttgc ctcttcctcc      180
tcctgtccgg ggcccgcccg cgctcgggtg ggggtgctgt gatgcgtgag gcagccgggg      240
gaggcccgga gtccgagact gcttgagcgc tgcgcacacc cctctcgtgg gccccccacg      300
```

```
taggtgcggg aacctggttg aaccccaagc tgataggaag atgtcttcag gaaatgctaa      360
aattgggcac cctgccccca acttcaaagc cacagctgtt atgccagatg gtcagtttaa      420
agatatcagc ctgtctgact acaaaggaaa atatgttgtg ttcttctttt accctcttga      480
cttcaccttt gtgtgcccca cggagatcat tgctttcagt gatagggcag aagaatttaa      540
gaaactcaac tgccaagtga ttggtgcttc tgtggattct cacttctgtc atctagcatg      600
ggtcaataca cctaagaaac aaggaggact gggacccatg aacattcctt ggtatcaga       660 cccgaagcgc accattgctc aggattatgg ggtcttaaag gctgatgaag gcatctcgtt      720
caggggcctt tttatcattg atgataaggg tattcttcgg cagatcactg taaatgacct      780
ccctgttggc cgctctgtgg atgagacttt gagactagtt caggccttcc agttcactga      840
caaacatggg gaagtgtgcc cagctggctg gaaacctggc agtgatacca tcaagcctga      900
tgtccaaaag agcaaagaat atttctccaa gcagaagtga gcgctgggct gttttagtgc      960
caggctgcgg tgggcagcca tgagaacaaa accctcttctg tattttttttt ttccattagt     1020 aaaacacaag acttcagatt cagccgaatt gtggtgtctt acaaggcagg cctttcctac     1080
agggggtgga gagaccagcc tttcttcctt tggtaggaat ggcctgagtt ggcgttgtgg      1140
gcaggctact ggtttgtatg atgtattagt agagcaaccc attaatcttt tgtagtttgt     1200
attaaacttg aactgagacc ttgatgagtc tttaaaaaaa aaaaaaaaaa aaaaaaaaa      1260 aa                                                                      1262

<210> SEQ ID NO 6
<211> LENGTH: 1593
<212> TYPE: DNA
<213> ORGANISM: Homo sapiens

<400> SEQUENCE: 6
gcggtgccct tgcggcgcag ctggggtcgc ggccctgctc ccgcgctttt cttaaggccc       60
gcgggcggcg caggagcggc actcgtggct gtggtggctt cggcagcggc ttcagcagat      120
cggcggcatc agcggtagca ccagcactag cagcatgttg agccgggcag tgtgcggcac      180
cagcaggcag ctggctccgg ttttgggggta tctgggctcc aggcagaagc acagcctccc     240
cgacctgccc tacgactacg gcgccctgga acctcacatc aacgcgcaga tcatgcagct      300
gcaccacagc aagcaccacg cggcctacgt gaacaacctg aacgtcaccg aggagaagta      360
ccaggaggcg ttggccaagg gagatgttac agcccagata gctcttcagc ctgcactgaa      420
gttcaatggt ggtggtcata tcaatcatag cattttctgg acaaacctca gccctaacgg      480
tggtggagaa cccaaagggg agttgctgga agccatcaaa cgtgactttg gttcctttga      540
caagtttaag gagaagctga cggctgcatc tgttggtgtc caaggctcag gttgggttg       600 gcttggtttc aataaggaac ggggacactt acaaattgct gcttgtccaa atcaggatcc      660
actgcaagga acaacaggcc ttattccact gctggggatt gatgtgtggg agcacgctta      720
ctaccttcag tataaaaatg tcaggcctga ttatctaaaa gctatttgga atgtaatcaa      780
ctgggagaat gtaactgaaa gatacatggc ttgcaaaaag taaaccacga tcgttatgct      840
gagtatgtta agctctttat gactgttttt gtagtggtat agagtactgc agaatacagt      900
aagctgctct attgtagcat tcttgatgt tgcttagtca cttatttcat aaacaactta       960
atgttctgaa taatttctta ctaaacattt tgttattggg caagtgattg aaaatagtaa     1020
atgctttgtg tgattgaatc tgattggaca ttttcttcag agagctaaat tacaattgtc     1080
atttataaaa ccatcaaaaa tattccatcc atatactttg gggacttgta gggatgcctt     1140
```

| | |
|---|---|
| tctagtccta ttctattgca gttatagaaa atctagtctt ttgccccagt tacttaaaaa | 1200 |
| taaaatatta acactttccc aagggaaaca ctcggctttc tatagaaaat tgcacttttt | 1260 |
| gtcgagtaat cctctgcagt gatacttctg gtagatgtca cccagtggtt tttgttaggt | 1320 |
| caaatgttcc tgtatagttt ttgcaaatag agctgtatac tgtttaaatg tagcaggtga | 1380 |
| actgaactgg ggtttgctca cctgcacagt aaaggcaaac ttcaacagca aaactgcaaa | 1440 |
| aaggtggttt ttgcagtagg agaaaggagg atgtttattt gcagggcgcc aagcaaggag | 1500 |
| aattgggcag ctcatgcttg agacccaatc tccatgatga cctacaagct agagtattta | 1560 |
| aaggcagtgg taaatttcag gaaagcagaa gtt | 1593 |

<210> SEQ ID NO 7
<211> LENGTH: 1024
<212> TYPE: DNA
<213> ORGANISM: Homo sapiens

<400> SEQUENCE: 7

| | |
|---|---|
| cttcctggct cctccttcct ccccacccct ctaataggct cataagtggg ctcaggcctc | 60 |
| tctgcgggc tcactctgcg cttcaccatg gctttcattg ccaagtcctt ctatgacctc | 120 |
| agtgccatca gcctggatgg ggagaaggta gatttcaata cgttccgggg cagggccgtg | 180 |
| ctgattgaga atgtggcttc gctctgaggc acaaccaccc gggacttcac ccagctcaac | 240 |
| gagctgcaat gccgctttcc caggcgcctg gtggtccttg gcttcccttg caaccaattt | 300 |
| ggacatcagg agaactgtca gaatgaggag atcctgaaca gtctcaagta tgtccgtcct | 360 |
| gggggtggat accagcccac cttcaccctt gtccaaaaat gtgaggtgaa tgggcagaac | 420 |
| gagcatcctg tcttcgccta cctgaaggac aagctcccct acccttatga tgacccattt | 480 |
| tccctcatga ccgatcccaa gctcatcatt tggagccctg tgcgccgctc agatgtggcc | 540 |
| tggaactttg agaagttcct catagggccg gagggagagc ccttccgacg ctacagccgc | 600 |
| accttcccaa ccatcaacat tgagcctgac atcaagcgcc tccttaaagt tgccatatag | 660 |
| atgtgaactg ctcaacacac agatctccta ctccatccag tcctgaggag ccttaggatg | 720 |
| cagcatgcct tcaggagaca ctgctggacc tcagcattcc cttgatatca gtccccttca | 780 |
| ctgcagagcc ttgcctttcc cctctgcctg tttccttttc ctctcccaac cctctggttg | 840 |
| gtgattcaac ttgggctcca agacttgggt aagctctggg ccttcacaga atgatggcac | 900 |
| cttcctaaac cctcatgggt ggtgtctgag aggcgtgaag ggcctggagc cactctgcta | 960 |
| gaagagacca ataagggca ggtgtggaaa cggcaaaaaa aaaaaaaaa aaaaaaaaa | 1020 |
| aaaa | 1024 |

<210> SEQ ID NO 8
<211> LENGTH: 1779
<212> TYPE: DNA
<213> ORGANISM: Homo sapiens

<400> SEQUENCE: 8

| | |
|---|---|
| gtcgccccgg gacggggagg tggggagctg agggcaagtc gcgcccgccc ctgaaatccc | 60 |
| agccgcctag cgattggctg caagggtctc ggcttggccg cggattggtc cacacccgagg | 120 |
| gcttgaaagg tggctgggag cgccggacac ctcagacgga cggtggccag ggatcaggca | 180 |
| gcggctcagg cgaccctgag tgtgccccca cccgccatg gccggctgc tgcaggcgtc | 240 |
| ctgcctgctt tccctgctcc tggccggctt cgtctcgcag agccggggac aagagaagtc | 300 |

| | |
|---|---:|
| gaagatggac tgccatggtg gcataagtgg caccatttac gagtacggag ccctcaccat | 360 |
| tgatggggag gagtacatcc ccttcaagca gtatgctggc aaatacgtcc tctttgtcaa | 420 |
| cgtggccagc tactgaggcc tgacgggcca gtacattgaa ctgaatgcac tacaggaaga | 480 |
| gcttgcacca ttcggtctgg tcattctggg cttttccctgc aaccaatttg gaaaacagga | 540 |
| accaggagag aactcagaga tccttcctac cctcaagtat gtccgaccag gtggaggctt | 600 |
| tgtccctaat ttccagctct tgagaaagg ggatgtcaat ggagagaaag agcagaaatt | 660 |
| ctacactttc ctaaagaact cctgtcctcc cacctcggag ctcctgggta catctgaccg | 720 |
| cctcttctgg gaacccatga aggttcacga catccgctgg aactttgaga agttcctggt | 780 |
| ggggccagat ggtatacccca tcatgcgctg gcaccaccgg accacggtca gcaacgtcaa | 840 |
| gatggacatc ctgtcctaca tgaggcggca ggcagccctg ggggtcaaga ggaagtaact | 900 |
| gaaggccgtc tcatcccatg tccaccatgt aggggaggga ctttgttcag aagaaatcc | 960 |
| gtgtctccaa ccacactatc tacccatcac agacccctt cctatcactc aaggccccag | 1020 |
| cctggcacaa atggatgcat acagttctgt gtactgccag gcatgtgggt gtgggtgcat | 1080 |
| gtgggtgttt acacacatgc ctacaggtat gcgtgattgt gtgtgtgtgc atgggtgtac | 1140 |
| agccacgtgt ctacctatgt gtcttttctgg gaatgtgtac catctgtgtg cctgcagctg | 1200 |
| tgtagtgctg gacagtgaca acccttctc tccagttctc cactccaatg ataatagttc | 1260 |
| acttacacct aaacccaaag gaaaaccag ctctaggtcc aattgttctg ctctaactga | 1320 |
| tacctcaacc ttggggccag catctcccac tgcctccaaa tattagtaac tatgactgac | 1380 |
| gtccccagaa gtttctgggt ctaccacact ccccaacccc ccactcctac ttcctgaagg | 1440 |
| gccctcccaa ggctacatcc ccaccccaca gttctccctg agagagatca acctccctga | 1500 |
| gatcaaccaa ggcagatgtg acagcaaggg ccacggaccc catggcaggg gtggcgtctt | 1560 |
| catgagggag gggcccaaag cccttgtggg cggacctccc ctgagcctgt ctgaggggcc | 1620 |
| agcccttagt gcattcaggc taaggcccct gggcagggat gccacccctg ctccttcgga | 1680 |
| ggacgtgccc tcacccctca ctggtccact ggcttgagac tcaccccgtc tgcccagtaa | 1740 |
| aagccttct gcagcagctg aaaaaaaaaa aaaaaaaa | 1779 |

<210> SEQ ID NO 9
<211> LENGTH: 735
<212> TYPE: DNA
<213> ORGANISM: Homo sapiens

<400> SEQUENCE: 9

| | |
|---|---:|
| gcggtgtccg gcagtagagc tcgctgcaga tccgggctct gaccatgatt tggcgccgcg | 60 |
| cggcgctggc ggggacgcgg ctggtttgga gcaggagcgg ctcggcaggc tggcttgaca | 120 |
| gggcggcggg agctgcggga gctgcggcag ctgcggcctc tgggatggag agcaatacat | 180 |
| catcatcttt ggagaattta gcgacggcgc ctgtgaacca gatccaagaa acaatttctg | 240 |
| ataattgtgt ggtgattttc tcaaaaacat cctgttctta ctgtacaatg gcaaaaaagc | 300 |
| ttttccatga catgaatgtt aactataaag tggtggaact ggacctgctt gaatatggaa | 360 |
| accagttcca agatgctctt tacaaaatga ctggtgaaag aactgttcca agaatatttg | 420 |
| tcaatggtac ttttattgga ggtgcaactg acactcatag gcttcacaaa gaaggaaaat | 480 |
| tgctcccact agttcatcag tgttattaa aaaaaagtaa gaggaaagaa tttcagtgat | 540 |
| gtttatacta ataagtttgc tagtacagtg tcagttattt aaagtggtaa tgcccgataa | 600 |
| tgtcttttaa atgtttgagg atgttttaaa tacatgcatt gtcttcacga agaagatgta | 660 |

| | |
|---|---:|
| aaaataatga acaataaatt gcggtggaaa cctcaaaaaa aaaaaaaaaa aaaaaaaaaa | 720 |
| aaaaaaaaaa aaaaa | 735 |

<210> SEQ ID NO 10
<211> LENGTH: 827
<212> TYPE: DNA
<213> ORGANISM: Homo sapiens

<400> SEQUENCE: 10

| | |
|---|---:|
| gcagtggagg cggcccaggc ccgccttccg cagggtgtcg ccgctgtgcc gctagcggtg | 60 |
| ccccgcctgc tgcggtggca ccagccagga ggcggagtgg aagtggccgt ggggcgggta | 120 |
| tgggactagc tggcgtgtgc gccctgagac gctcagcggg ctatatactc gtcggtgggg | 180 |
| ccggcggtca gtctgcggca gcggcagcaa gacggtgcag tgaaggagag tgggcgtctg | 240 |
| gcggggtccg cagtttcagc agagccgctg cagccatggc cccaatcaag gtgggagatg | 300 |
| ccatcccagc agtggaggtg tttgaagggg agccagggaa caaggtgaac ctggcagagc | 360 |
| tgttcaaggg caagaagggt gtgctgtttg agttcctgg ggccttcacc cctggatgtt | 420 |
| ccaaggttcg gctcctggct gatcccactg gggcctttgg gaaggagaca gacttattac | 480 |
| tagatgattc gctggtgtcc atctttggga atcgacgtct caagaggttc tccatggtgg | 540 |
| tacaggatgg catagtgaag gccctgaatg tggaaccaga tggcacaggc ctcacctgca | 600 |
| gcctggcacc caatatcatc tcacagctct gaggcctcgg gccagattac ttcctccacc | 660 |
| cctccctatc tcacctgccc agccctgtgc tggggccctg caattggaat gttggccaga | 720 |
| tttctgcaat aaacacttgt ggtttgcggc aaaaaaaaaa aaaaaaaaaa aaaaaaaaaa | 780 |
| aaaaaaaaaa aaaaaaaaaa aaaaaaaaaa aaaaaaaaaa aaaaaaa | 827 |

<210> SEQ ID NO 11
<211> LENGTH: 3174
<212> TYPE: DNA
<213> ORGANISM: Homo sapiens

<400> SEQUENCE: 11

| | |
|---|---:|
| tcctcctggg tcttgcctag cggcgggcgc atgcttagtc accgtgaggc tgcgcttgcc | 60 |
| cggggcccgc gcccccctac cccggggacc gccccgggc cgcccgcccc acttggcgcg | 120 |
| ccacttccgc gtgcatggcc ctgctgcccc gagccctgag cgccggcgcg ggaccgagct | 180 |
| ggcggcgggc ggcgcgcgcc ttccgaggct tcctgctgct tctgcccgag cccgcggccc | 240 |
| tcacgcgcgc cctctcccgt gccatggcct gcaggcagga gccgcagccg cagggcccgc | 300 |
| cgcccgctgc tggcgccgtg gcctcctatg actacctggt gatcggggc ggctcgggcg | 360 |
| ggctggccag cgcgcgcagg gcggccgagc tgggtgccag ggccgccgtg gtggagagcc | 420 |
| acaagctggg tggcacttgc gtgaatgttg atgtgtacc caaaaaggta atgtggaaca | 480 |
| cagctgtcca ctctgaattc atgcatgatc atgctgatta tggctttcca agttgtgagg | 540 |
| gtaaattcaa ttggcgtgtt attaaggaaa agcgggatgc ctatgtgagc cgcctgaatg | 600 |
| ccatctatca aaacaatctc accaagtccc atatagaaat catccgtggc catgcagcct | 660 |
| tcacgagtga tcccaagccc acaatagagg tcagtggaa aaagtacacc gccccacaca | 720 |
| tcctgatcgc cacaggtggt atgccctcca cccctcatga gagccagatc cccggtgcca | 780 |
| gcttaggaat aaccagcgat ggatttttc agctggaaga attgcccggc cgcagcgtca | 840 |
| ttgttggtgc aggttacatt gctgtggaga tggcagggat cctgtcagcc ctgggttcta | 900 |

```
agacatcact gatgatacgg catgataagg tacttagaag ttttgattca atgatcagca    960
ccaactgcac ggaggagctg gagaacgctg gcgtggaggt gctgaagttc tcccaggtca   1020
aggaggttaa aaagactttg tcgggcttgg aagtcagcat ggttactgca gttcccggta   1080
ggctaccagt catgaccatg attccagatg ttgactgcct gctctgggcc attgggcggg   1140
tcccgaatac caaggacctg agtttaaaca aactgggat tcaaaccgat gacaagggtc    1200
atatcatcgt agacgaattc cagaatacca acgtcaaagg catctatgca gttgggatg    1260 tatgtggaaa agctcttctt actccagttg caatagctgc tggccgaaaa cttgcccatc   1320 gacttttga atataaggaa gattccaaat tagattataa caacatccca actgtggtct    1380
tcagccaccc ccctattggg acagtgggac tcacggaaga tgaagccatt cataaatatg   1440
gaatagaaaa tgtgaagacc tattcaacga gctttacccc gatgtatcac gcagttacca   1500
aaaggaaaac aaaatgtgtg atgaaaatgg tctgtgctaa caaggaagaa aaggtggttg   1560
ggatccatat gcagggactt gggtgtgatg aaatgctgca gggttttgct gttgcagtga   1620
agatgggagc aacgaaggca gactttgaca acacagtcgc cattcaccct acctcttcag   1680
aagagctggt cacacttcgt tgagaaccag gagacacgtg tggcgggcag tgggacccat   1740
agatcttctg aaatgaaaca aataatcaca ttgacttact gtttgagttt tatgtatttc   1800
tttattttaa tcaggatctt ctgatagtgg aaattttag tacataatag aacttattta   1860
tggagttaga aatttgtagt gttatccagg attgattttc atttgatcac atctcacagt   1920
aattaatatt ttcaagtttt tttttatta acagctctgt gctagttttt tttttctgtt    1980
ttagcctcat cccaaatata aagctttgtg aagtacaatt aacttaatgt acttgaatga   2040
atagaacttg ctactttttt tttttttttt tttgagacag agttttgctc tcattgccca   2100
ggctggagtg cggtggtgct atttcagctc accacaacct ctgcctcctg ggttcaagtg   2160
attctcctgc cttagcctcc cgaatagctg gaattacagg cacgcaccac catgcctgac   2220 taatttgta ttttagtag acatggggtt tctccatgtt ggtcaggctg gtctcaaact     2280
cccaccttca ggtgatccgc ccacctcggc ctcctgaggt gctgagatta caggcgtgag   2340
ccactgtgcc agcttgctaa ttttcacaga agttgatggc aattcttcac atgtaaacag   2400
tgccagtgca cagaaccttt atatatttt tgaagccagt actgtgctct gcatataaca    2460
aagctgcttc aaggatgaga ccttttctcta aaagcatgta atgtgagaag ccggcctgcc   2520
ttattttctt ttttctttt taatgattaa aaatagtttg tggcaaggca cggtggctca    2580
ggcctgtaat tctagcactt tgggaggccg aggcaggagg attacttgag cctacaagtt   2640
tgaggccagc atgcacagca tagcaagact gcatctctac agagagtaaa aaaaattacc   2700
cgagtgtggt gatgtgcatc tgtaatctca gctacttggg aggctgaggt gagaggatca   2760
cttgagcttg ggtgaggtga ggctgcagtg agtcctgatc atgctgctgc actcaatctt   2820
ggacaacaga gcaagaccct gtctcaaaaa aaaaaaaaa aatatatat atatatatat     2880 attattttta tgaggtgaag tgcatcaaac ttggaaaaga tttgaggagg ctgggaacct   2940
cctggaaaac cactccttga agaaagatat gagagacatt tagaagtgat tcctgctttc   3000
agaaggaggt ggattcaaat acatcaaaag tcccttcctc tgctaagtgt ttatagttca   3060
atgaataatt tcaatatttg tatgtgttct tgtcatttta tttttttctg aaaaacttcc   3120
aaaaatttga aataaaatt acagcctttt cttcttataa aaaaaaaaa aaaa           3174
```

<210> SEQ ID NO 12
<211> LENGTH: 1661

```
<212> TYPE: DNA
<213> ORGANISM: Homo sapiens

<400> SEQUENCE: 12
attgcattcc tgggcattgc taactagtga agtataccag atggaaatgt cttcgaagct      60
gtccctttaa aactcgagca agctaccagg caaactccgc ctccagggag gttccttatt     120
aaataggagc caactggctg ggtcggggct caataccca agcataccct gcaactgagg      180
attcttcccg gggagaccgc agcccatcgg catggctcaa gagtttgtga actgcaaaat     240
ccagcctggg aaggtggttg tgttcatcaa gcccacctgc ccgtactgca ggagggccca    300
agagatcctc agtcaattgc ccatcaaaca agggcttctg gaatttgtcg atatcacagc     360
caccaaccac actaacgaga ttcaagatta tttgcaacag ctcacgggag caagaacggt     420
gcctcgagtc tttattggta aagattgtat aggcggatgc agtgatctag tctctttgca     480
acagagtggg gaactgctga cgcggctaaa gcagattgga gctctgcagt aaccacagaa     540
caggccccat gctgacgtcc ctcctcaaga gctggatggc attgcaaatg atgacagcac     600
ttctggtgga tgaatttggg ggcacaaaca gcttttttcc tcttttggct cagtatttaa     660
aagtggacca acttgctctt aatcacaggg ccaagaaggt tgacgggcca tcttggtttt     720
cttctggatg tgctctttgg ttttcagaag actgtgacaa gttctggccc aggattcgct     780
cactgaccct caattgtcct cttggcatg cgtttcttac tgttctccat gtgtcggcat      840
gtctctacct ctaagccagt gttttcaac tatgtttatc cagactcctt ctccacaatg      900
atgaatccac agttggttat ctgctactgc ccattagcta aaatcatttt gctgcttgac     960
tttatggagt ttgtattatg aaatcagtgg gtattttgaa tgtgttcttt ctaactacat    1020
gcatctctcc actcaactcc accccatccc atcccacctt gaaaatcact gctctgaacc    1080
agtgttctcc accttgtcct ccacagatct cataggaaat gttcaacaat tctgtgaaag    1140
gtcacaggac ccaattggag aaatcatatg aaaagcatag ttggtcttgg tgtcatatgg    1200
atcagaggca caagtgcaga ggctgtggtc atgcggaaca ctctgttatt taagatggct    1260
atccagataa tcctgaacac tgtgtatta ttttatttag actaccagca aagattaaag     1320
catgaaatgt aaaacatctg ataaaactta cagcccccta caccaagagt gtatctgtga    1380
aagagctcct acactttgaa aacttaagaa tcccttatca tgaagtttgc ctgttctaga    1440
attgtaagat tgttaatttc cttcaatctc tagtgacaac acttaatttc ttttctaata    1500
aaaaaaccct atagatgatt cagtgatttt tgtccaattc atttgcatgt tctcaagaca    1560
ttaaggaatg ttatgcgaaa tacactaact taaaactgtg tttatatttg gccctgccat    1620
tataaataaa gacacgtgct gctgtcaaaa aaaaaaaa a                          1661

<210> SEQ ID NO 13
<211> LENGTH: 1039
<212> TYPE: DNA
<213> ORGANISM: Homo sapiens

<400> SEQUENCE: 13
gctcgtccgc tccctccccc gcgccgtgca cgtcttggtt cgggccgggc ataaaaggct      60
tcgcggccca gggctcactt ggcgctgaga acgcgggtcc acgcgtgtga tcgtccgtgc     120
gtctagcctt tgcccacgca gctttcagtc atggcctccg gtaacgcgcg catcggaaag     180
ccagcccctg acttcaaggc cacagcggtg gttgatggcg ccttcaaaga ggtgaagctg     240
tcggactaca agggaagta cgtggtcctc ttttctacc ctctggactt cactttttgtg      300
```

| | |
|---|---|
| tgccccaccg agatcatcgc gttcagcaac cgtgcagagg acttccgcaa gctgggctgt | 360 |
| gaagtgctgg gcgtctcggt ggactctcag ttcacccacc tggcttggat caacacccc | 420 |
| cggaaagagg gaggcttggg cccctgaac atcccctgc ttgctgacgt gaccagacgc | 480 |
| ttgtctgagg attacggcgt gctgaaaaca gatgagggca ttgcctacag gggcctcttt | 540 |
| atcatcgatg gcaagggtgt ccttcgccag atcactgtta atgatttgcc tgtgggacgc | 600 |
| tccgtggatg aggctctgcg gctggtccag gccttccagt acacagacga gcatggggaa | 660 |
| gtttgtcccg ctggctggaa gcctggcagt gacacgatta gcccaacgt ggatgacagc | 720 |
| aaggaatatt tctccaaaca caattaggct ggctaacgga tagtgagctt gtgcccctgc | 780 |
| ctaggtgcct gtgctgggtg tccacctgtg cccccacctg ggtgccctat gctgacccag | 840 |
| gaaaggccag acctgcccct ccaaactcca cagtatggga ccctggaggg ctaggccaag | 900 |
| gccttctcat gcctccacct agaagctgaa tagtgacgcc ctcccccaag cccacccagc | 960 |
| cgcacacagg cctagaggta accaataaag tattagggaa aggtgtgaaa aaaaaaaaa | 1020 |
| aaaaaaaaaa aaaaaaaaa | 1039 |

<210> SEQ ID NO 14
<211> LENGTH: 2799
<212> TYPE: DNA
<213> ORGANISM: Homo sapiens

<400> SEQUENCE: 14

| | |
|---|---|
| acgtgtgcgg gagggaagca ggaagtgact gcgggagtgg agccggcgag agagtggcag | 60 |
| cggggggctga tggaagtgca gtgggggctg gagagggcac cctactgtat ccagcatgct | 120 |
| ccaaggccac agctctgtgt tccaggcctt gctggggacc ttcttcacct gggggatgac | 180 |
| agcagctggg gcagctctcg tgttcgtatt ctctagtgga cagaggcgga tcttagatgg | 240 |
| aagtcttggc tttgctgcag gggtcatgtt ggcagcttcc tattggtctc ttctggcccc | 300 |
| agcagttgag atggccacgt cctctgggg cttcggtgcc tttgccttct ccctgtggc | 360 |
| tgttggcttc acccttggag cggcttttgt ctacttggct gacctcctga tgcctcactt | 420 |
| gggtgcagca gaagaccccc agacgaccct ggcactgaac ttcggctcta cgttgatgaa | 480 |
| gaagaagtct gatcctgagg gtcccgcgct gctcttccct gagagtgaac tttccatccg | 540 |
| gataggtaga gctgggcttc tttcagacaa gagtgagaat ggtgaggcat atcagagaaa | 600 |
| gaaggcggca gccactggcc ttccagaggg tcctgctgtc cctgtgcctt ctcgagggaa | 660 |
| tctggcacag cccggcggca gcagctggag gaggatcgca ctgctcatct tggccatcac | 720 |
| tatacacaac gttccagagg gtctcgctgt tggagttgga tttggggcta tagaaaagac | 780 |
| ggcatctgct acctttgaga gtgccaggaa tttggccatt ggaatcggga tccagaattt | 840 |
| ccccgagggc ctggctgtca gccttccctt gcgaggggca ggcttctcca cctggagagc | 900 |
| tttctggtat gggcagctga gcggcatggt ggagcccctg gccgggtct ttggtgcctt | 960 |
| tgccgtggtg ctggctgagc ccatcctgcc ctacgctctg gcctttgctg ccggtgccat | 1020 |
| ggtctacgtg gtcatggacg acatcatccc cgaagcccag atcagtggta atgggaaact | 1080 |
| ggcatcctgg gcctccatcc tgggatttgt agtgatgatg tcactggacg ttggcctggg | 1140 |
| ctagggctga gacgcttcgg acccgggaa aggccatacg aagaaacagc agtggttggc | 1200 |
| ttctatggga caacaagctt cttcttcac attaaaactt ttttccttcc tctcttcttc | 1260 |
| atctcattat cctgattgac tctgattata atagaaccat ttttactttg ctttgaggga | 1320 |
| gattttgat ttaatgggga attttaaggt gtcatggaaa tacagattct tgttttggc | 1380 |

-continued

```
cactgaatgg actctctctt cagtgggatt atcaaggaac ttcagatcag ggaaatctcc    1440
acttcgggac cttctatctg cctcccaact cctcaaggtc acctatagaa gcgagctacc    1500
aaaagacgtc tcctaagcat tttggtggcc tagtgactca gggcagagtg gccagcacac    1560
ctctcatccg cccctcctgc tccatcactg ctgagcctct ccccatctag aatgttggaa    1620
ctggagcatc ataaagatag caagctacct tccaaggccg agccagccca gagaggagca    1680
tgtcttcctt tacctccccc taaggagata ctacatggga gggggacaca gaaaaaggga    1740
aggaaattgg ctagtctggc ttttttttt ttttttttta aaggcaaaga ttgacattat     1800
tgaaggaaag gggatgagga caactgtgaa ctcacagtga gccctgtgga agaagagac     1860 agacagagtg tgggtttgtt cggaggcctc tgctgtcaat ggattccagg agcaaggcca    1920
tttgtcgcgc tttccaaatt tcttaggcat ttattttgat aagtttatag ccatcatgtt    1980
tctaagagac ttggagacac cagcaaactg ctagaactca aactcttcaa ttactcaaag    2040
aaggagccat ttcagttaac tcaagtgaat gaaagagttt tggaatctgc tgtgggtcct    2100
tccctgttga ccatttggta acttataatc tgacaaaaac tcttgagctg caacaggcct    2160
tgccagaggg ctcaggatgg gaaggaaga agggatagg aaaagaagag gtaattttac      2220
atttcccctt taaagtaaat tttagccaac tcatcattct gaaatgtccc tataaagaat    2280
gagtcgaact agaccagaag ccagcctact ccttcttaca tagcttctcc aacagggta     2340 gcaatgacct gtccacttca aacacagata aggcctgcca tcctcattgg ttaaaggcac    2400
acgtgagact ttcagtgggc tctgctgaga aggaaggcag cccaggagtc aggtatgcag    2460
gcattgcatt gtcagtgtct gctctcagag tttacacatt caattgcttc caagggtgaa    2520
tctcctgctc tgtgaatgct atcagacccc aaaggccaac cttgggctgg gtctatgtac    2580
gttcttccga agcactgatg atcaaaattg aagacacatt cagaggtttg attggttgag   2640
attaactggt gtggtggttg gtgtatgtat gttttatttt tatgtctttg tatgtagttc    2700
tacataatgc aaattgtgct ttctgatgga caagacctca taactgtgat taatatcaat    2760
aaaaagggga tgttgtggat gaaaaaaaa aaaaaaaa                              2799
```

<210> SEQ ID NO 15
<211> LENGTH: 508
<212> TYPE: DNA
<213> ORGANISM: Homo sapiens

<400> SEQUENCE: 15

```
tttggtgctt tggatccatt tccatcggtc cttacagccg ctcgtcagac tccagcagcc      60
aagatggtga agcagatcga gagcaagact gcttttcagg aagccttgga cgctgcaggt    120
gataaacttg tagtagttga cttctcagcc acgtggtgtg ggccttgcaa aatgatcaag    180
cctttctttc attccctctc tgaaaagtat tccaacgtga tattccttga agtagatgtg    240
gatgactgtc aggatgttgc ttcagagtgt gaagtcaaat gcatgccaac attccagttt    300
tttaagaagg gacaaaaggt gggtgaattt tctggagcca ataaggaaaa gcttgaagcc    360
accattaatg aattagtcta atcatgtttt ctgaaaatat aaccagccat tggctatta     420 aaacttgtaa ttttttaat ttacaaaaat ataaatatg aagacataaa cccagttgcc      480
atctgcgtga caataaaaca ttaatgct                                         508
```

<210> SEQ ID NO 16
<211> LENGTH: 1591
<212> TYPE: DNA

<213> ORGANISM: Homo sapiens

<400> SEQUENCE: 16

| | | | | | |
|---|---|---|---|---|---|
| ccctgcgtct | ctgcccgccc | cgtggcgccc | gagtgcactg | aagatggcgg | ctgctgtagg | 60 |
| acggttgctc | cgagcgtcgg | ttgcccgaca | tgtgagtgcc | attccttggg | gcatttctgc | 120 |
| cactgcagcc | ctcaggcctg | ctgcatgtgg | aagaacgagc | ttgacaaatt | tattgtgttc | 180 |
| tggttccagt | caagcaaaat | tattcagcac | cagttcctca | tgccatgcac | ctgctgtcac | 240 |
| ccagcatgca | ccctatttta | agggtacagc | cgttgtcaat | ggagagttca | aagacctaag | 300 |
| ccttgatgac | tttaagggga | aatatttggt | gcttttcttc | tatcctttgg | atttcacctt | 360 |
| tgtgtgtcct | acagaaattg | ttgcttttag | tgacaaagct | aacgaatttc | acgacgtgaa | 420 |
| ctgtgaagtt | gtcgcagtct | cagtggattc | ccactttagc | catcttgcct | ggataaatac | 480 |
| accaaggaag | aatggtggtt | tgggccacat | gaacatcgca | ctcttgtcag | acttaactaa | 540 |
| gcagatttcc | cgagactacg | gtgtgctgtt | agaaggttct | ggtcttgcac | taagaggtct | 600 |
| cttcataatt | gaccccaatg | gagtcatcaa | gcatttgagc | gtcaacgatc | tcccagtggg | 660 |
| ccgaagcgtg | gaagaaaccc | tccgcttggt | gaaggcgttc | cagtatgtag | aaacacatgg | 720 |
| agaagtctgc | ccagcgaact | ggacaccgga | ttctcctacg | atcaagccaa | gtccagctgc | 780 |
| ttccaaagag | tactttcaga | aggtaaatca | gtagatcacc | catgtgtatc | tgcaccttct | 840 |
| caactgagag | aagaaccaca | gttgaaacct | gcttttatca | ttttcaagat | ggttatttgt | 900 |
| agaaggcaag | gaaccaatta | tgcttgtatt | cataagtatt | actctaaatg | ttttgttttt | 960 |
| gtaattctgg | ctaagacctt | ttaaacatgg | ttagttgcta | gtacaaggaa | tcctttattg | 1020 |
| gtaacatctt | ggtggctggc | tagctagttt | ctacagaaca | taatttgcct | ctatagaagg | 1080 |
| ctattcttag | atcatgtctc | aatggaaaca | ctcttcttc | ttagccttac | ttgaatcttg | 1140 |
| cctataataa | agtagagcaa | cacacattga | aagcttctga | tcaacggtcc | tgaaattttc | 1200 |
| atcttgaatg | tctttgtatt | aaactgaatt | ttcttttaag | ctaacaaaga | tcataatttt | 1260 |
| caatgattag | ccgtgtaact | cctgcaatga | atgtttatgt | gattgaagca | aatgtgaatc | 1320 |
| gtattatttt | aaaaagtggc | agagtgactt | aactgatcat | gcatgatccc | tcatccctga | 1380 |
| aattgagttt | atgtagtcat | tttacttatt | ttattcatta | gctaactttg | tctatgtata | 1440 |
| tttctagata | ttgattagtg | taatcgatta | taaaggatat | ttatcaaatc | cagggattgc | 1500 |
| attttgaaat | tataattatt | ttctttgctg | aagtattcat | tgtaaaacat | acaaaataaa | 1560 |
| catattttaa | aacatttgca | ttttaccacc | a | | | 1591 |

<210> SEQ ID NO 17
<211> LENGTH: 1246
<212> TYPE: DNA
<213> ORGANISM: Homo sapiens

<400> SEQUENCE: 17

| | | | | | |
|---|---|---|---|---|---|
| gtctttgccc | tcgcgacgcc | gccacctccg | gaacaagcca | tggtggcggc | gacggtggca | 60 |
| gcggcgtggc | tgctcctgtg | ggctgcggcc | tgcgcgcagc | aggagcagga | cttctacgac | 120 |
| ttcaaggcgg | tcaacatccg | gggcaaactg | gtgtcgctgg | agaagtaccg | cggatcggtg | 180 |
| tccctggtgg | tgaatgtggc | cagcgagtgc | ggcttcacag | accagcacta | ccgagccctg | 240 |
| cagcagctgc | agcgagacct | gggcccccac | cactttaacg | tgctcgcctt | ccctgcaac | 300 |
| cagtttggcc | aacaggagcc | tgacagcaac | aaggagatta | gagctttgc | ccgccgcacc | 360 |
| tacagtgtct | cattccccat | gtttagcaag | attgcagtca | ccggtactgg | tgcccatcct | 420 |

```
gccttcaagt acctggccca gacttctggg aaggagccca cctggaactt ctggaagtac    480
ctagtagccc cagatggaaa ggtggtaggg gcttgggacc caactgtgtc agtggaggag    540
gtcagacccc agatcacagc gctcgtgagg aagctcatcc tactgaagcg agaagactta    600
taaccaccgc gtctcctcct ccaccacctc atcccgccca cctgtgtggg gctgaccaat    660
gcaaactcaa atggtgcttc aaagggagag acccactgac tctccttcct ttactcttat    720
gccattggtc ccatcattct gtgggggaa aaattctagt attttgatta tttgaatctt    780
acagcaacaa ataggaactc ctggccaatg agagctcttg accagtgaat caccagccga    840
tacgaacgtc ttgccaacaa aaatgtgtgg caaatagaag tatatcaagc aataatctcc    900
cacccaaggc ttctgtaaac tgggaccaat gattacctca tagggctgtt gtgaggatta    960
ggatgaaata cctgtgaaag tgcctaggca gtgccagcca ataggaggc attcaatgaa   1020 cattttttgc atataaacca aaaataact tgttatcaat aaaacttgc atccaacatg    1080 aatttccagc cgatgataat ccaggccaaa ggtttagttg ttgttatttc ctctgtatta   1140
ttttcttcat tacaaaagaa atgcaagttc attgtaacaa tccaaacaat acctcacgat   1200
ataaaataaa aatgaaagta tcctcctcaa aaaaaaaaaa aaaaaa                  1246

<210> SEQ ID NO 18
<211> LENGTH: 1342
<212> TYPE: DNA
<213> ORGANISM: Homo sapiens

<400> SEQUENCE: 18
gaggaagtga cgacaggcgt gcccttgaca ggcagggagg gctaggctgt gcatccctcc     60
gctcgcattg cagggagatg gctcagcgac ttcttctgag gaggttcctg gcctctgtca    120
tctccaggaa gccctctcag ggtcagtggc caccctcac ttccagagcc ctgcagaccc    180
cacaatgcag tcctggtggc ctgactgtaa cacccaaccc agcccggaca atatacacca    240
cgaggatctc cttgacaacc tttaatatcc aggatggacc tgactttcaa gaccgagtgg    300
tcaacagtga gacaccagtg gttgtggatt tccacgcaca gtggtgtgga ccctgcaaga    360
tcctggggcc gaggttagag aagatggtgg ccaagcagca cgggaaggtg gtgatggcca    420
aggtggatat tgatgaccac acagacctcg ccattgagta tgaggtgtca gcggtgccca    480
ctgtgctggc catgaagaat ggggacgtgg tggacaagtt tgtgggcatc aaggatgagg    540
atcagttgga ggccttcctg aagaagctga ttggctgaca agcaggatg agtcctggtt    600 cccttgcccg cgtgggaccc caatagaact cagcccttcc atgccagccc ttcctgctgc    660
ctccctcctg tctggctcct ggggcccatg cttagagccc aggctccagc cctgagtgct    720
tccgagctgg cggactgccc aggggccatc agaggatggt ggtgctgctg ctgatccggg    780
gaccgctgtc ttccctccca tacgcctttc atccctcctt ctagggccta tggcagttct    840
cccaggatgt gtggcgagag cctgggccag cccacagcgt tcctagtcag gcagccacac    900
cttggtcctc atcttggtcc cttccaatct gaaacctcgt gcctggctcg tctgccacct    960
acatttctct ttccagctgc tgttttgtaa aagaaaaag aaaaagaag cccaaactag   1020 tgagagtaat atctaattat ctcatttttt gtaggtctgt gataaagaac ttagtcatcc   1080
cttccacctc ctactgtgaa gaacagaccc tgggtcccac actgaaatcc cctctagtca   1140
cccattccca cccccagggg agctgcctcc caggcagggg gtgcagaaaa tgattgatgg   1200
gctggggaac cctggagagc ctcgactccg gaagtctcaa ggtgcctcct cctctcctta   1260
```

```
gctggcccgt tggttttctg agcagggggc tgaactgtga acaagtcaga caaataaagc    1320
aagggtctgc accatcaaaa aa                                             1342
```

<210> SEQ ID NO 19
<211> LENGTH: 921
<212> TYPE: DNA
<213> ORGANISM: Homo sapiens

<400> SEQUENCE: 19

```
gcggcgctcg cgccaaggga cgtgtttctg cgctcgcgtg gtcatggagg cgctgccgct     60
gctagccgcg acaactccgg accacggccc ccaccgaagg ctgcttctgc tgccgctact    120
gctgttcctg ctgccggctg agctgtgcag ggctgggag acagaggaga ggccccggac     180
tcgcgaagag gagtgccact tctacgcggg tggacaagtg tacccgggag aggcatcccg    240
ggtatcggtc gccgaccact ccctgcacct aagcaaagcg aagatttcca agccagcgcc    300
ctactgggaa ggaacagctg tgatcgatgg agaatttaag gagctgaagt taactgatta    360
tcgtgggaaa tacttggttt tcttcttcta cccacttgat ttcacatttg tgtgtccaac    420
tgaaattatc gcttttggcg acagacttga agaattcaga tctataaata ctgaagtggt    480
agcatgctct gttgattcac agtttaccca tttggcctgg attaataccc ctcgaagaca    540
aggaggactt gggccaataa ggattccact tctttcagat ttgacccatc agatctcaaa    600
ggactatggt gtatacctag aggactcagg ccacactctt agaggtctct tcattattga    660
tgacaaagga atcctaagac aaattactct gaatgatctt cctgtgggta gatcagtgga    720
tgagacacta cgtttggttc aagcattcca gtacactgac aaaacacggag aagtctgccc    780
tgctggctgg aaacctggta gtgaaacaat aatcccagat ccagctggaa agctgaagta    840
tttcgataaa ctgaattgag aaatacttct tcaagttatg atgcttgaaa gttctcaata    900
aagttcacgg tttcattacc a                                              921
```

<210> SEQ ID NO 20
<211> LENGTH: 1200
<212> TYPE: DNA
<213> ORGANISM: Homo sapiens

<400> SEQUENCE: 20

```
cagttaaaag gaggcgcctg ctggcctccc cttacagtgc ttgttcgggg cgctccgctg     60
gcttcttgga caattgcgcc atgtgtgctg ctcggctagc ggcggcggcg gcggcggccc    120
agtcggtgta tgccttctcg gcgcgcccgc tggccggcgg ggagcctgtg agcctgggct    180
ccctgcgggg caaggtacta cttatcgaga atgtggcgtc cctctgaggc accacggtcc    240
gggactacac ccagatgaac gagctgcagc ggcgcctcgg accccggggc ctggtggtgc    300
tcggcttccc gtgcaaccag tttgggcatc aggtgcgccg gcggagcgg ggcggggcgg    360
gggcggacgt gcagtagtgg ctgggggcgc cggcggtgtg ctggtgggtg ccgtcggctc    420
catgcgcgga gagtctggct actctctcgt ttcctttctg ttgctcgtag ctgctgaaat    480
tcctctccgc ccttgggatt gcgcatggag ggcaaaatcc cggtgactca tagaaaatct    540
cccttgtttg tggttagaac gtttctctcc tcctcttgac cccgggttct agctgccctt    600
ctctcctgta ggagaacgcc aagaacgaag agattctgaa ttccctcaag tacgtccggc    660
ctggtggtgg gttcgagccc aacttcatgc tcttcgagaa gtgcgaggtg aacggtgcgg    720
gggcgcaccc tctcttcgcc ttcctgcggg aggccctgcc agctcccagc gacgacgcca    780
ccgcgcttat gaccgacccc aagctcatca cctggtctcc ggtgtgtcgc aacgatgttg    840
```

```
cctggaactt tgagaagttc ctggtgggcc ctgacggtgt gccectacgc aggtacagcc    900
gccgcttcca gaccattgac atcgagcctg acatcgaagc cctgctgtct caagggccca    960
gctgtgccta gggcgcccct cctacccegg ctgcttggca gttgcagtgc tgctgtctcg   1020
gggggttttt catctatgag ggtgtttcct ctaaacctac gagggaggaa cacctgatct   1080
tacagaaaat accacctcga gatgggtgct ggtcctgttg atcccagtct ctgccagacc   1140
aaggcgagtt tccccactaa taaagtgccg ggtgtcagca gaaaaaaaaa aaaaaaaaa    1200
```

<210> SEQ ID NO 21
<211> LENGTH: 1274
<212> TYPE: DNA
<213> ORGANISM: Homo sapiens

<400> SEQUENCE: 21

```
gcttctgtct ggcggcggca gcatggcggc ggggcggct gaggcagctg tagcggccgt     60
ggaggaggtc ggctcagccg ggcagtttga ggagctgctg cgcctcaaag ccaagtccct    120
ccttgtggtc catttctggg caccatgggc tccacagtgt gcacagatga acgaagttat    180
ggcagagtta gctaaagaac tccctcaagt ttcatttgtg aagttggaag ctgaaggtgt    240
tcctgaagta tctgaaaaat atgaaattag ctctgttccc acttttctgt ttttcaagaa    300
ttctcagaaa atcgaccgat tagatggtgc acatgcccca gagttgacca aaaaagttca    360
gcgacatgca tctagtggct ccttcctacc cagcgctaat gaacatctta agaagatct     420
caaccttcgc ttgaagaaat tgactcatgc tgcccectgc atgctgttta tgaaaggaac    480
tcctcaagaa ccacgctgtg gtttcagcaa gcagatggtg gaaattcttc acaaacataa    540
tattcagttt agcagttttg atatcttctc agatgaagag gttcgacagg gactcaaagc    600
ctattccagt tggcctacct atcctcagct ctatgtttct ggagagctca taggaggact    660
tgatataatt aaggagctag aagcatctga agaactagat acaatttgtc ccaaagctcc    720
caaattagag gaaaggctca agtgctgac aaataaagct tctgtgatgc tctttatgaa    780
aggaaacaaa caggaagcaa atgtggatt cagcaaacaa attctggaaa tactaaatag    840
tactggtgtt gaatatgaaa cattcgatat attggaggat gaagaagttc ggcaaggatt    900
aaaagcttac tcaaattggc caacataccc tcagctgtat gtgaaagggg agctggtggg    960
aggattggat attgtgaagg aactgaaaga aaatggtgaa ttgctgccta tactgagagg   1020
agaaaattaa taaatcttaa acttggtgcc caactattgt aagaaatatt taattacatt   1080
gggagcagtt catgatttag tcctcagaaa tggactagga atagaaaatt cctgctttct   1140
cagttacatg ttttgtgtat ttcacaatgt cgtgctaaat aaatgtatgt tacattttt    1200
tcccaccaaa aatagaatgc aataaacatc ttcaaattat taacgaaaaa aaaaaaaaa    1260
aaaaaaaaaa aaaa                                                    1274
```

<210> SEQ ID NO 22
<211> LENGTH: 710
<212> TYPE: DNA
<213> ORGANISM: Homo sapiens

<400> SEQUENCE: 22

```
gctcgtccgc tcctccccc gcgccgtgca cgtcttggtt cgggccgggc ataaaaggct     60
tcgcggccca gggctcactt ggcgctgaga acgcgggtcc acgcgtgtga tcgtccgtgc    120
gtctagcctt tgcccacgca gctttcagtc atggcctccg gtaacgcgcg catcggaaag    180
```

```
ccagcccctg acttcaaggc cacagcggtg gttgatggcg ccttcaaaga ggtgaagctg    240
tcggactaca aagggaagta cgtggtcctc ttttttctacc ctctggactt cacttttgtg   300
tgccccaccg agatcatcgc gttcagcaac cgtgcagagg acttccgcaa gctgggctgt    360
gaagtgctgg cgtctcggt ggactctcag ttcacccacc tggcttggta tgagcagggg     420
ccaaagaggg aggttgcagc taagctcaca ccctcaggtc ctagcagtgt ggcttcgtgg    480
ccattgctca acctctggaa cctgcgtttc cccatcgtga aaataatgga aacattgccg    540
cccaagtctt taaggatgat gacagtaatt agcatttgac aactagttgc ctggtatata    600
gagttgcaga tgcaactcag atgcaactct atctactcta tgtacttagt tcccaggagg    660
gaggctgtgc tgccctattt catgaagatg gaaactccag ttcaccgaag                710

<210> SEQ ID NO 23
<211> LENGTH: 1715
<212> TYPE: DNA
<213> ORGANISM: Homo sapiens

<400> SEQUENCE: 23
gaaccaaccg gttgcttgct gtcccagcgg cgccccctca tcaccgtcgc catgcccgga    60
ggtctgcttc tcgggacgt ggctcccaac tttgaggcca ataccaccgt cggccgcatc     120
cgtttccacg actttctggg agactcatgg ggcattctct tctcccaccc tcgggacttt    180 acccagtgt gcaccacaga gcttggcaga gctgcaaagc tggcaccaga atttgccaag    240
aggaatgtta agttgattgc cctttcaata gacagtgttg aggaccatct tgcctggagc    300
aaggatatca atgcttacaa ttgtgaagag cccacagaaa agttaccttt tcccatcatc    360
gatgatagga atcgggagct tgccatcctg ttgggcatgc tggatccagc agagaaggat    420
gaaaagggca tgcctgtgac agtccgtgtg gtgtttgttt tggtcctga taagaagctg    480 aagctgtcta tcctctaccc agctaccact ggcaggaact tgatgagat tctcagggta    540 gtcatctctc tccagctgac agcagaaaaa agggttgcca ccccagttga ttggaaggat    600
ggggatagtg tgatggtcct tccaaccatc cctgaagaag aagccaaaaa acttttcccg    660
aaaggagtct tcaccaaaga gctcccatct ggcaagaat acctccgcta cacaccccag    720
ccttaagtct cttggagaag ctggtgctgt gagccagagg atgtcagctg ccaattgtgt    780
tttcctgcag caattccata acacatcct ggtgtcatca cagccaaggt ttttaggttg    840
ctataccaat ggcttattaa atgaaaatgg cactaaaagt ttcttgagat tctttatact    900
ctctgccttc agcaatcaat tccattcata catcagcact ctgctggttc tgtttgaaat    960
atgttctgta tttaaaactc aaatcttgtt ggatctctgc agggcttgtg accaatgaag    1020
tcatatttgt tgatggttga caaagcttgc ttcactccat cagagaatga ctatcaattt    1080 tttttttaact gtcctatcac gtcctctcct gtcacccatt ttgaagagtg gcagaacttg    1140
aagttcaact tcctctgtaa atatccaagt ataaagccca ggaacttcta gaataaccca    1200
gatgcgcttt aatttttttt aatatgtttt gatcacagaa cttctagaat aacccagatg    1260
ctctttcata ttcttttaat acatcttgat cacagctggg ggaaaaaaag cttttttaatt    1320 ctataccttc ctagtagata agtgaagagc agggaaagag acctttaaat attttgctat    1380
aaaaaaattt gtgataagtt tctatcaaaa tggggagatt gcagaaaagg cttcccttgg    1440
ctcccaagga ggtgtagcag gtgtgagcaa tattagtgcc atgtgccttt cacacagggt    1500
ttgcatttat cagtctgttt tccgatgatg tgtacatgaa agagtacacc atgtgaagag    1560
aagagagaat gattgaaaat gttttagtat agaactcttc ttgcagtggg ttgctatttt    1620
```

| | |
|---|---:|
| ctagattttta cttttttaggg aacaaaataa aatcctttgt taaaactggg aaaaaaaaaa | 1680 |
| aaaaaaaaaa aaaaaaaaaa aaaaaaaaaa aaaaa | 1715 |

<210> SEQ ID NO 24
<211> LENGTH: 1182
<212> TYPE: DNA
<213> ORGANISM: Homo sapiens

<400> SEQUENCE: 24

| | |
|---|---:|
| aatgagggcc tccagggggc gggtcggact gccgcgggcc ggggagcgct ctgggtggcc | 60 |
| agctgtgggc ccgggccgtc gtgggctccg gcttgcgtgc ggagatgagc gggtccctcg | 120 |
| gccgagctgc ggcggctctg ctccgctggg ggcgcggcgc gggcggcggt ggcctttggg | 180 |
| gtccgggcgt gcgggcggcg ggctcggcg cgggcggcgg cggctcggcg gagcagttgg | 240 |
| acgcgctggt gaagaaggac aaggtggtgg tcttcctcaa ggggacgccg gagcagcccc | 300 |
| agtgcggctt cagcaacgcc gtggtgcaga tcctgcggct gcacggcgtc cgcgattacg | 360 |
| cggcctacaa cgtgctggac gacccggagc tccgacaagg cattaaagac tattccaact | 420 |
| ggcccaccat cccgcaagtg tacctcaatg gcgagtttgt aggggggctgt gacattcttc | 480 |
| tgcagatgca ccagaatggg gacttggtgg aagaactgaa aaagctgggg atccactccg | 540 |
| ccctttttaga tgaaaagaaa gaccaagact ccaagtgagg gcggccaagt cctcgctgag | 600 |
| cagagaggga gccgttcatg tcagagactc actgccagaa aagccttacc cattttggtt | 660 |
| ttcactattg agaccgcaac tgcttgcact gatcattttg gttcgtgagc agttggtgat | 720 |
| tttagttggt ctggtgttcg ggctaagaat attttattgt ggacttaatt acaaccactg | 780 |
| cactgtaatg attcaatgct gtattatgat attgctgtaa acaaaattca ttcttatatt | 840 |
| gtcacttatt ctttgcctga ttcagaagtt aaataggagc tttggaatca ttattcatga | 900 |
| cccctctgca aatgtgtcag tctccaaaga gagtatctcc ccccaaattt tgtgtagctt | 960 |
| cttttgttat ggaaaatggt gaacaaaaa agaaactgtg ataactgggg cgttgttttt | 1020 |
| taaaataaac tccagcacag ggatgctgtg catgcctgag ttgattccga agtgcatatg | 1080 |
| tctgtaagga tttggagtgc ctgcagtgtt ttatgtgtgg gaagtaaggg tgagtctcat | 1140 |
| attcttctat taaatttgcc acaagaattg caaaaaaaa aa | 1182 |

<210> SEQ ID NO 25
<211> LENGTH: 1170
<212> TYPE: DNA
<213> ORGANISM: Homo sapiens

<400> SEQUENCE: 25

| | |
|---|---:|
| aaggctatta ttaccaccac tgagtggctt aaataatcct gtcaacagca atcgcccatt | 60 |
| tccaaagcca tggtgaaaca tctctgtgct aatttctttt gttttgtttc ctaattttt | 120 |
| ttttttggca ggtggtggga aataatcttt gtcttctttg gagtaaacct tcaacaccgg | 180 |
| atttttttctt ttaattatgg atgtaaaccc caatatcccc ataatttaca ttgggtctcg | 240 |
| accaattgcc taattataag aggatatatt taggctctta tttcatccac acaaaaactt | 300 |
| gtgtaacagg tagttggaaa catctgaggc accactttga ttctgttttg atggtcatg | 360 |
| ttttttctcc tccgtttccc cagcatgtct gccaccatcc tcatgcactg cttccaagtg | 420 |
| cctgggagcc tttatgagcg tccctaaacc taaaagaatc cagaggcggg gctcggatga | 480 |
| accctcgaga taagcaagtg agccgcttct cccctctaaa ggatgtttac acgtgggtgg | 540 |

```
cactcgctgg aatccagcgc tcgggcagcc ctgggaggac gcgctcagct gcgaggagga      600
tggagagcaa tacatcatca tctttggaga atttagcgac ggcgcctgtg aaccagatcc      660
aagaaacaat ttctgataat tgtgtggtga ttttctcaaa acatcctgt tcttactgta       720 caatggcaaa aaagcttttc catgacatga atgttaacta taaagtggtg aactggacc       780 tgcttgaata tggaaaccag ttccaagatg ctctttacaa aatgactggt gaaagaactg     840
ttccaagaat atttgtcaat ggtacttta ttggaggtgc aactgacact cataggcttc      900
acaaagaagg aaaattgctc ccactagttc atcagtgtta tttaaaaaaa agtaagagga      960
aagaatttca gtgatgttta tactaataag tttgctagta cagtgtcagt tatttaaagt     1020
ggtaatgccc gataatgtct tttaaatgtt tgaggatgtt ttaaatacat gcattgtctt     1080
cacgaagaag atgtaaaaat aatgaacaat aaattgcggt ggaaacctaa aaaaaaaaa      1140 aaaaaaaaaa aaaaaaaaa aaaaaaaaa                                         1170

<210> SEQ ID NO 26
<211> LENGTH: 964
<212> TYPE: DNA
<213> ORGANISM: Homo sapiens

<400> SEQUENCE: 26
gagcgctctg gagggcgtgg ccgtgggaaa ggaggcgcgg aaagccgacg cgcgtccatt       60
ggtcggctgg acgaggggag gagccgctgg ctcccagccc cgccgcgatg agcctcggcc      120
gcctttgccg cctactgaag ccggcgctgc tctgtggggc tctggccgcg cctggcctgg      180
ccgggaccat gtgcgcgtcc cgggacgact ggcgctgtgc gcgctccatg cacgagtttt      240
ccgccaagga catcgacggg cacatggtta acctggacaa gtaccggggc ttcgtgtgca      300
tcgtcaccaa cgtggcctcc cagtgaggca agaccgaagt aaactacact cagctcgtcg      360
acctgcacgc ccgatacgct gagtgtggtt tgcggatcct ggccttcccg tgtaaccagt      420
tcggaaagca ggagccaggg agtaacgaag agatcaaaga gttcgccgcg ggctacaacg      480
tcaaattcga tatgttcagc aagatctgcg tgaacgggga cgacgcccac ccgctgtgga      540
agtggatgaa gatccaaccc aagggcaagg gcatcctggg aaatgccatc aagtggaact      600
tcaccaagtt tggacaccgt ctctccacag ttcctcatcg acaagaacgg ctgcgtggtg      660
aagcgctacg gacccatgga ggagcccctg gtgatagaga aggacctgcc ccactatttc      720
tagctccaca agtgtgtggc cccgcccgag cccctgccca cgcccttgga gccttccacc      780
ggcactcatg acggcctgcc tgcaaacctg ctggtggggc agacccgaaa atccagcgtg      840
caccccgccg gaggaaggtc ccatggcctg ctgggcttgg ctcggcgccc ccaccctgg      900 ctaccttgtg ggaataaaca gacaaattag cctgctggaa aaaaaaaaaa aaaaaaaaaa      960
aaaa                                                                     964

<210> SEQ ID NO 27
<211> LENGTH: 1031
<212> TYPE: DNA
<213> ORGANISM: Homo sapiens

<400> SEQUENCE: 27
agtcctgact acggcctccg ggcccttttgt ccccgctagc ggcgctcggg gtggggagc        60 caggaggggc gggagacggg cgggtatggg ccgcgcgggc gcaggctccc ccgggcgccg      120
caggcagcgc tgccagagcc ggggcaggcg gcggccgcga gccctcggc ggcggaaggc       180 cccagcgtgc aggcgcagga gggcgcggcg ccggcggaag aagccctgtc cccgcagctt      240
```

```
gcgaccggag atccacgaat gtcccaagtc caggacccg tgcgcgtccc gggacgactg    300
gcgctgtgcg cgctccatgc acgagttttc cgccaaggac atcgacgggc acatggttaa    360
cctggacaag taccggggct tcgtgtgcat cgtcaccaac gtggcctccc agtgaggcaa    420
gaccgaagta aactacactc agctcgtcga cctgcacgcc cgatacgctg agtgtggttt    480
gcggatcctg gccttcccgt gtaaccagtt cgggaagcag gagccaggga gtaacgaaga    540
gatcaaagag ttcgccgcgg gctacaacgt caaattcgat atgttcagca agatctgcgt    600
gaacggggac gacgcccacc cgctgtggaa gtggatgaag atccaaccca agggcaaggg    660
catcctggga aatgccatca agtggaactt caccaagttc ctcatcgaca gaacggctg    720 cgtggtgaag cgctacggac ccatggagga gcccctggtg atagagaagg acctgcccca    780
ctatttctag ctccacaagt gtgtggcccc gcccgagccc ctgccacgc ccttggagcc    840 ttccaccggc actcatgacg gcctgcctgc aaacctgctg gtggggcaga cccgaaaatc    900
cagcgtgcac cccgccggag gaaggtccca tggcctgctg gcttggctc ggcgccccca    960 cccctggcta ccttgtggga ataaacagac aaattagcct gctggaaaaa aaaaaaaaaa   1020
aaaaaaaaaa a                                                         1031

<210> SEQ ID NO 28
<211> LENGTH: 1236
<212> TYPE: DNA
<213> ORGANISM: Homo sapiens

<400> SEQUENCE: 28
actctcgcga gatccctact ggctataaag gcagcgcccc ggagagctct tgcgcgtctt     60
gttcttgcct ggtgtcggtg gttagtttct gcgacttgtg ttgggactgg tgagtgtggg    120
cagtgcggcc cctgcggagt gaggcgcggc gcgcccttct tgcctgttgc ctcttcctcc    180
tcctgtccgg ggcccgcccg cgctcgggtg ggggtgctgt gatgcgtgag cagccgggg    240 gaggcccgga gtccgagact gcttgagcgc tgcgcacacc cctctcgtgg gccccccacg    300
tagctgatag gaagatgtct tcaggaaatg ctaaaattgg gcaccctgcc cccaacttca    360
aagccacagc tgttatgcca gatggtcagt ttaaagatat cagcctgtct gactacaaag    420
gaaaatatgt tgtgttcttc tttttacccctc ttgacttcac ctttgtgtgc cccacggaga    480
tcattgcttt cagtgatagg gcagaagaat ttaagaaact caactgccaa gtgattggtg    540
cttctgtgga ttctcacttc tgtcatctag catgggtcaa tacacctaag aaacaaggag    600
gactgggacc catgaacatt cctttggtat cagacccgaa gcgcaccatt gctcaggatt    660
atggggtctt aaaggctgat gaaggcatct cgttcagggg ccttttttatc attgatgata    720 agggtattct tcggcagatc actgtaaatg acctccctgt tggccgctct gtggatgaga    780
ctttgagact agttcaggcc ttccagttca ctgacaaaca tggggaagtg tgcccagctg    840
gctgaaaacc tggcagtgat accatcaagc ctgatgtcca aaagagcaaa gaatatttct    900
ccaagcagaa gtgagcgctg ggctgttttta gtgccaggct gcggtgggca gccatgagaa    960 caaaaccctct tctgtatttt ttttttccat tagtaaaaca caagacttca gattcagccg   1020
aattgtggtg tcttacaagg caggcctttc ctacaggggg tggagagacc agcctttctt   1080
cctttggtag gaatggcctg agttggcgtt gtgggcaggc tactggtttg tatgatgtat   1140
tagtagagca accattaat ctttttgtagt ttgtattaaa cttgaactga gaccttgatg   1200
agtctttaaa aaaaaaaaa aaaaaaaaa aaaaaa                                1236
```

<210> SEQ ID NO 29
<211> LENGTH: 1042
<212> TYPE: DNA
<213> ORGANISM: Homo sapiens

<400> SEQUENCE: 29

| | | | | | |
|---|---|---|---|---|---|
| actctcgcga | gatccctact | ggctataaag | gcagcgcccc | ggagagctct | tgcgcgtctt | 60 |
| gttcttgcct | ggtgtcggtg | gttagtttct | gcgacttgtg | ttgggactgc | tgataggaag | 120 |
| atgtcttcag | gaaatgctaa | aattgggcac | cctgccccca | acttcaaagc | cacagctgtt | 180 |
| atgccagatg | gtcagtttaa | agatatcagc | ctgtctgact | acaaaggaaa | atatgttgtg | 240 |
| ttcttctttt | accctcttga | cttcaccttt | gtgtgcccca | cggagatcat | tgctttcagt | 300 |
| gatagggcag | aagaatttaa | gaaactcaac | tgccaagtga | ttggtgcttc | tgtggattct | 360 |
| cacttctgtc | atctagcatg | ggtcaataca | cctaagaaac | aaggaggact | gggacccatg | 420 |
| aacattcctt | tggtatcaga | cccgaagcgc | accattgctc | aggattatgg | ggtcttaaag | 480 |
| gctgatgaag | gcatctcgtt | cagggggcctt | tttatcattg | atgataaggg | tattcttcgg | 540 |
| cagatcactg | taaatgacct | ccctgttggc | cgctctgtgg | atgagacttt | gagactagtt | 600 |
| caggccttcc | agttcactga | caaacatggg | gaagtgtgcc | cagctggctg | gaaacctggc | 660 |
| agtgatacca | tcaagcctga | tgtccaaaag | agcaaagaat | atttctccaa | gcagaagtga | 720 |
| gcgctgggct | gttttagtgc | caggctgcgg | tgggcagcca | tgagaacaaa | acctcttctg | 780 |
| tattttttt | ttccattagt | aaaacacaag | acttcagatt | cagccgaatt | gtggtgtctt | 840 |
| acaaggcagg | cctttcctac | aggggtgga | gagaccagcc | tttcttcctt | tggtaggaat | 900 |
| ggcctgagtt | ggcgttgtgg | gcaggctact | ggtttgtatg | atgtattagt | agagcaaccc | 960 |
| attaatcttt | tgtagtttgt | attaaacttg | aactgagacc | ttgatgagtc | tttaaaaaaa | 1020 |
| aaaaaaaaaa | aaaaaaaaaa | aa | | | | 1042 |

<210> SEQ ID NO 30
<211> LENGTH: 1035
<212> TYPE: DNA
<213> ORGANISM: Homo sapiens

<400> SEQUENCE: 30

| | | | | | |
|---|---|---|---|---|---|
| gcggtgccct | tgcggcgcag | ctggggtcgc | ggccctgctc | cccgcgcttt | cttaaggccc | 60 |
| gcgggcggcg | caggagcggc | actcgtggct | gtggtggctt | cggcagcggc | ttcagcagat | 120 |
| cggcggcatc | agcggtagca | ccagcactag | cagcatgttg | agccgggcag | tgtgcggcac | 180 |
| cagcaggcag | ctggctccgg | ttttgggggta | tctgggctcc | aggcagaagc | acagcctccc | 240 |
| cgacctgccc | tacgactacg | cgccctgga | acctcacatc | aacgcgcaga | tcatgcagct | 300 |
| gcaccacagc | aagcaccacg | cggcctacgt | gaacaacctg | aacgtcaccg | aggagaagta | 360 |
| ccaggaggcg | ttggccaagg | gagatgttac | agcccagata | gctcttcagc | ctgcactgaa | 420 |
| gttcaatggt | ggtggtcata | tcaatcatag | cattttctgg | acaaacctca | gccctaacgg | 480 |
| tggtggagaa | cccaaagggg | agttgctgga | agccatcaaa | cgtgactttg | gttccttttga | 540 |
| caagtttaag | gagaagctga | cggctgcatc | tgttggtgtc | caaggctcag | gttgggggttg | 600 |
| gcttggtttc | aataaggaac | ggggacactt | acaaattgct | gcttgtccaa | atcaggatcc | 660 |
| actgcaagga | acaacaggcc | ttattccact | gctggggatt | gatgtgtggg | agcacgctta | 720 |
| ctaccttcag | tataaaaatg | tcaggcctga | ttatctaaaa | gctatttgga | atgtaatcaa | 780 |
| ctgggagaat | gtaactgaaa | gatacatggc | ttgcaaaaag | taaaccacga | tcgttatgct | 840 |

```
gatcataccc taatgatccc agcaagataa tgtcctgtct tctaagatgt gcatcaagcc      900
tggtacatac tgaaaaccct ataaggtcct ggataatttt tgtttgatta ttcattgaag      960
aaacatttat tttccaattg tgtgaagttt ttgactgtta ataaagaat ctgtcaacca     1020 tcaaaaaaaa aaaaa                                                      1035
```

<210> SEQ ID NO 31
<211> LENGTH: 918
<212> TYPE: DNA
<213> ORGANISM: Homo sapiens

<400> SEQUENCE: 31

```
gcggtgccct tgcggcgcag ctggggtcgc ggccctgctc cccgcgcttt cttaaggccc       60
gcgggcggcg caggagcggc actcgtggct gtggtggctt cggcagcggc ttcagcagat      120
cggcggcatc agcggtagca ccagcactag cagcatgttg agccgggcag tgtgcggcac      180
cagcaggcag ctggctccgg ttttggggta tctgggctcc aggcagaagc acagcctccc      240
cgacctgccc tacgactacg gcgccctgga acctcacatc aacgcgcaga tcatgcagct      300
gcaccacagc aagcaccacg cggcctacgt gaacaacctg aacgtcaccg aggagaagta      360
ccaggaggcg ttggccaagg gggagttgct ggaagccatc aaacgtgact ttggttcctt      420
tgacaagttt aaggagaagc tgacggctgc atctgttggt gtccaaggct caggttgggg      480
ttggcttggt ttcaataagg aacggggaca cttacaaatt gctgcttgtc caaatcagga      540
tccactgcaa ggaacaacag gccttattcc actgctgggg attgatgtgt gggagcacgc      600
ttactacctt cagtataaaa atgtcaggcc tgattatcta aaagctattt ggaatgtaat      660
caactgggag aatgtaactg aaagatacat ggcttgcaaa aagtaaacca cgatcgttat      720
gctgatcata ccctaatgat cccagcaaga taatgtcctg tcttctaaga tgtgcatcaa      780
gcctggtaca tactgaaaac cctataaggt cctggataat ttttgtttga ttattcattg      840
aagaaacatt tattttccaa ttgtgtgaag tttttgactg ttaataaaag aatctgtcaa      900
ccatcaaaaa aaaaaaaa                                                   918
```

<210> SEQ ID NO 32
<211> LENGTH: 18
<212> TYPE: DNA
<213> ORGANISM: Artificial sequence
<220> FEATURE:
<223> OTHER INFORMATION: sense oligonucleotide for CAT

<400> SEQUENCE: 32

```
cgcagttcgg ttctccac                                                    18
```

<210> SEQ ID NO 33
<211> LENGTH: 18
<212> TYPE: DNA
<213> ORGANISM: Artificial sequence
<220> FEATURE:
<223> OTHER INFORMATION: antisense oligonucleotide for CAT

<400> SEQUENCE: 33

```
gggtcccgaa ctgtgtca                                                    18
```

<210> SEQ ID NO 34
<211> LENGTH: 20
<212> TYPE: DNA
<213> ORGANISM: Artificial sequence
<220> FEATURE:

```
<223> OTHER INFORMATION: sense oligonucleotide for SOD1

<400> SEQUENCE: 34
gcatcatcaa tttcgagcag                                              20

<210> SEQ ID NO 35
<211> LENGTH: 20
<212> TYPE: DNA
<213> ORGANISM: Artificial sequence
<220> FEATURE:
<223> OTHER INFORMATION: antisense oligonucleotide for SOD1

<400> SEQUENCE: 35
caggccttca gtcagtcctt                                              20

<210> SEQ ID NO 36
<211> LENGTH: 19
<212> TYPE: DNA
<213> ORGANISM: Artificial sequence
<220> FEATURE:
<223> OTHER INFORMATION: sense oligonucleotide for GPX1

<400> SEQUENCE: 36
caaccagttt gggcatcag                                               19

<210> SEQ ID NO 37
<211> LENGTH: 19
<212> TYPE: DNA
<213> ORGANISM: Artificial sequence
<220> FEATURE:
<223> OTHER INFORMATION: antisense oligonucleotide for GPX1

<400> SEQUENCE: 37
gttcacctcg cacttctcg                                               19

<210> SEQ ID NO 38
<211> LENGTH: 18
<212> TYPE: DNA
<213> ORGANISM: Artificial sequence
<220> FEATURE:
<223> OTHER INFORMATION: sense oligonucleotide for GPX4

<400> SEQUENCE: 38
tacggaccca tggaggag                                                18

<210> SEQ ID NO 39
<211> LENGTH: 22
<212> TYPE: DNA
<213> ORGANISM: Artificial sequence
<220> FEATURE:
<223> OTHER INFORMATION: antisense oligonucleotide for GPX4

<400> SEQUENCE: 39
ccacacactt gtggagctag aa                                           22

<210> SEQ ID NO 40
<211> LENGTH: 21
<212> TYPE: DNA
<213> ORGANISM: Artificial sequence
<220> FEATURE:
<223> OTHER INFORMATION: sense oligonucleotide for PRDX2

<400> SEQUENCE: 40
cactgacaaa catggggaag t                                            21
```

```
<210> SEQ ID NO 41
<211> LENGTH: 21
<212> TYPE: DNA
<213> ORGANISM: Artificial sequence
<220> FEATURE:
<223> OTHER INFORMATION: antisense oligonucleotide for PRDX2

<400> SEQUENCE: 41
tttgctcttt tggacatcag g                                            21

<210> SEQ ID NO 42
<211> LENGTH: 20
<212> TYPE: DNA
<213> ORGANISM: Artificial sequence
<220> FEATURE:
<223> OTHER INFORMATION: sense oligonucleotide for SO2

<400> SEQUENCE: 42
tccactgcaa ggaacaacag                                              20

<210> SEQ ID NO 43
<211> LENGTH: 19
<212> TYPE: DNA
<213> ORGANISM: Artificial sequence
<220> FEATURE:
<223> OTHER INFORMATION: antisense oligonucleotide for SOD2

<400> SEQUENCE: 43
taagcgtgct cccacacat                                               19

<210> SEQ ID NO 44
<211> LENGTH: 18
<212> TYPE: DNA
<213> ORGANISM: Artificial sequence
<220> FEATURE:
<223> OTHER INFORMATION: sense oligonucleotide for GPX2

<400> SEQUENCE: 44
gtccttggct tcccttgc                                                18

<210> SEQ ID NO 45
<211> LENGTH: 22
<212> TYPE: DNA
<213> ORGANISM: Artificial sequence
<220> FEATURE:
<223> OTHER INFORMATION: antisense oligonucleotide for GPX2

<400> SEQUENCE: 45
tgttcaggat ctcctcattc tg                                           22

<210> SEQ ID NO 46
<211> LENGTH: 19
<212> TYPE: DNA
<213> ORGANISM: Artificial sequence
<220> FEATURE:
<223> OTHER INFORMATION: sense oligonucleotide for GAPDH

<400> SEQUENCE: 46
agccacatcg ctcagacac                                               19

<210> SEQ ID NO 47
<211> LENGTH: 19
<212> TYPE: DNA
<213> ORGANISM: Artificial sequence
```

-continued

```
<220> FEATURE:
<223> OTHER INFORMATION: antisense oligonucleotide for GAPDH

<400> SEQUENCE: 47
gcccaatacg accaaatcc                                                    19
```

HEMOPATHY PROGNOSIS METHOD

This invention relates to a method for the prognosis of hemopathies, more particularly the personalized, or theranostic, prognosis of hemopathies.

Chronic myeloid leukemia is one of the blood diseases grouped under the name "myeloproliferative syndromes." It is characterized by an excessive and persistent production within the bone marrow of abnormal white blood cells (pathological polymorphonuclear neutrophils). Without the appropriate treatment, it develops into acute leukemia, characterized by the accumulation of immature cells in the bone marrow.

Chronic Myeloid Leukemia (CML) is a relatively rare disease since there are only around 600 new cases per year in France. It is slightly more frequent in men than women. Its frequency increases with age. At the time of diagnosis, the average age of patients is 53 years old.

The disease is linked to the appearance of an anomaly relating to a translocation between chromosomes 9 and 22 in bone marrow stem cells, causing the appearance of a small abnormal chromosome, the Philadelphia chromosome (from the name of town in the United States where the conference was held during which this chromosome anomaly was presented for the first time—in 1960). This anomaly leads to the wrong assembly of a gene of chromosome 9, called ABL, with a gene of chromosome 22, called BCR. This produces a gene called BCR-ABL, which is only present in pathological cells. This gene produces an abnormally high quantity of an enzyme, Abelson tyrosine kinase (ABL), responsible for the increased production of white blood cells carrying the Philadelphia chromosome.

Chronic myeloid leukemia develops in three phases:

The chronic phase

It is at this stage that the disease is diagnosed in most patients. During this phase, the leukemia develops slowly and there are very few or no symptoms at all. There are still only a few immature white blood cells (leukoblasts) in the bone marrow and in the blood. On average, this phase lasts for three to four years if left untreated.

The acceleration phase

This corresponds to an increase in the proportion of leukoblasts in the blood and bone marrow as well as an increase in the BCR-ABL load and the appearance of new chromosome anomalies. Non-specific symptoms are more frequent, such as tiredness, loss of appetite and a high temperature for no apparent reason. If treatment is not started, in a few months the disease develops into the acute, so-called transformation phase.

Transformation phase

From chronic, the leukemia then becomes acute. The bone marrow is invaded by leukoblasts and can no longer function properly. The prognosis for this secondary acute leukemia is very poor in the short term.

The therapeutic care of chronic myeloid leukemia lies in the administration of drugs called tyrosine kinase inhibitors.

The purpose of the treatment is to prevent acute transformation and its final aim is to eradicate BCR-ABL-expressing cells and prevent the transformation into acute leukemia.

During the chronic phase, the first-line treatment is imatinib mesylate (Glivec®). Other tyrosine kinase inhibitors, called second-generation inhibitors, have been developed after imatinib mesylate: nilotinib and dasatinib. They potentially cause serious side effects. Nilotib has been granted marketing authorization for first-line use.

The aim of the treatment is to obtain a major molecular response as quickly as possible in order to prevent clonal selection. This molecular response follows cytological and cytogenetic remission.

It is therefore necessary to provide the patient with an appropriate treatment as quickly as possible, enabling a fast major molecular response without causing a serious side effect. Several tyrosine kinase inhibitors exist and an inappropriate choice of treatment in the first year would moreover have a very high cost for the health system.

In order to optimize the therapeutic choices, methods of prognosis aimed in particular at assessing the risk of resistance to treatment with tyrosine kinase inhibitors (TKI) have been developed. One example of this is international application WO 2012/049329, which aims to predict a patient's response to a TKI treatment by measuring the kinase activity on different substrates.

However, such a method is difficult to implement simply and routinely.

Also, there is still a need to provide a method of personalized prognosis of CML since there is no marker that allows the therapeutic decision between a first-generation TKI treatment and a second- or subsequent-generation TKI treatment to be simply optimized.

One of the aims of this invention is to overcome these drawbacks.

Another aim of the invention is to propose a method of prognosis designed to minimize the risk of treatment failure.

Yet another aim of the invention is to reduce the cost of treatment by proposing at the outset the most appropriate treatment for the patient.

The invention also relates to an in vitro method of prognosis for the response to a treatment of an individual suffering from chronic myeloid leukemia, based on a leukemic biological sample taken from said individual, said method comprising:

a. a step of measuring the expression level of the genes from at least one subgroup of genes chosen from a group of genes,
   said group of genes consisting of 25 genes, said 25 genes comprising or being formed by the nucleic acid sequences SEQ ID NO: 1 to SEQ ID NO: 25,
   said subgroup consisting in 7 genes, said 7 genes comprising or being formed by the nucleic acid sequences SEQ ID NO: 1 to SEQ ID NO: 7,
   a value of the measured expression level being obtained for each of the genes of said subgroup, b. a step of comparing the value attributed to the preceding step with each of said genes of said subgroup to the value attributed to each of said genes of said subgroup obtained from a healthy biological sample, in order to obtain a ratio for each of said genes of said subgroup of the expression level in the leukemic biological sample to the expression level in the healthy sample, and c. a step of determining a score S according to the following Formula 1

$$S = \Sigma \text{ratio } i - \Sigma \text{ratio } j \quad \text{(Formula 1)}$$

where ratio i and ratio j represent respectively the ratios obtained for said genes of said subgroup comprising or being formed by the nucleic acid sequences SEQ ID NO: i or SEQ ID NO: j, where i and j are integers, i varying from 1 to 5 and j varying from 6 to 7, so that:

if S is less than 1, said individual will have more than around a 40% chance of having a major molecular remission one year after the start of treatment with a first-generation tyrosine kinase inhibitor, and if S is greater than or equal to 1, said individual will have less than around a 40% chance of having a major molecular remission one year after the start of treatment with a first-generation tyrosine kinase inhibitor.

In other words, the invention relates to an in vitro method for the prognosis of a response to a treatment of an individual suffering from chronic myeloid leukemia, based on a leukemic biological sample taken from said individual, said method comprising:

a. a step of measuring the quantity of complementary DNA corresponding to the genes of at least one subgroup of genes chosen from a group of genes,
said group of genes consisting of 25 genes, said 25 genes comprising or being formed by the nucleic acid sequences SEQ ID NO: 1 to SEQ ID NO: 25, said subgroup consisting in 7 genes, said 7 genes being identified by the molecules of nucleic acid comprising or being formed by the nucleic acid sequences SEQ ID NO: 1 to SEQ ID NO: 7,
a value of the expression level measured being obtained for each of the genes of said subgroup, b. a step of comparing the value attributed to the preceding step with each of said genes of said subgroup to the value attributed to each of said genes of said subgroup obtained from a healthy biological sample, in order to obtain a ratio for each of said genes of said subgroup of the expression level in the leukemic biological sample to the expression level in the healthy sample, and c. a step of determining a score S according to the following Formula 1

$$S = \Sigma \text{ratio } i - \Sigma \text{ratio } j \quad \text{(Formula 1)}$$

where ratio i and ratio j represent respectively the ratios obtained for said genes of said subgroup comprising or being formed by the nucleic acid sequences SEQ ID NO: i or SEQ ID NO: j, where i and j are integers, i varying from 1 to 5 and j varying from 6 to 7, so that:

if S is less than 1, said individual will have more than around a 40% chance of having a major molecular remission one year after the start of treatment with a first-generation tyrosine kinase inhibitor, and if S is greater than or equal to 1, said individual will have less than around a 40% chance of having a major molecular remission one year after the start of treatment with a first-generation tyrosine kinase inhibitor.

The invention is based on the surprising observation made by the inventor that at least 7 specific genes comprising or being formed of sequences SEQ ID NOS: 1 to 7, belonging to a group of 25 genes comprising or being formed of sequences SEQ ID NOS: 1 to 25 are sufficient to determine the prognosis, at 1 year, in other words one year after the start of treatment with a first-generation tyrosine kinase inhibitor, following the diagnosis of chronic myeloid leukemia, of patients suffering from chronic myeloid leukemia and treated with a first-generation tyrosine kinase inhibitor, i.e. treated with imatinib mesylate (Glivec®).

The 25 genes of the above-mentioned group are genes encoding enzymes participating in the detoxification of cells in which reactive oxygen species accumulate.

The method of the invention is implemented in the following manner:

from a sample taken from a patient, in particular a blood sample, the nucleic acids are extracted, preferably the ribonucleic acids (RNA), according to methods known to a person skilled in the art, the quantity of nucleic acids taken from said sample and that comprise or are formed of sequences SEQ ID NOS: 1 to 7 are measured; this measurement allows a value of the expression level for each of the said genes to be obtained, the value obtained for each of the preceding genes is compared with the value obtained for the same genes taken from a sample of an individual free of any hematologic disease, in order to obtain for each of said genes normalized values, or ratios, said normalized values are added together according to the above-mentioned Formula 1, which can be summarized by $$S = \Sigma \text{gene ratio SEQ ID NO: } i - \Sigma \text{gene ratio SEQ ID NO: } j$$

where i varies from 1 to 5 and j varies from 5 to 6, in order to obtain the score S, the prognosis is determined on the basis of the value obtained for the score S obtained at the preceding step.

In the invention, "a healthy biological sample" or "disease-free biological sample" means a sample of which the biological material that it contains comes from one or more healthy individuals, or is at least free of a hematological disease.

Advantageously, said healthy sample is of the same nature as the sample tested. In other words, if the sample tested is a blood sample, the healthy sample will also be a blood sample of another individual. Similarly, if the sample is a sample of bone marrow, the healthy sample will also be a sample of bone marrow.

It will be noted that although the healthy (or disease-free) sample can correspond to an assembly of samples taken from individuals free of hematological diseases, the patient's sample is unique and never corresponds to a mixture of samples taken from different patients.

Advantageously, the biological sample, and thus the biological sample taken from a healthy individual, is a sample of whole blood, of leukocytes, of circulating mononuclear cells or of bone marrow.

In the context of the invention, it is necessary to measure the expression level of the genes comprising or being formed by sequences SEQ ID NO: 1 to SEQ ID NO: 7. It is however possible, without this altering the prognostic response obtained, to measure the expression of one or more other genes of the group of genes comprising or being formed by sequences SEQ ID NOS: 8 to 25, which reflect the state of oxidation of the sample.

When the prognosis method of the invention is implemented, the score S allows the prognosis, and in particular the chances of survival, of a patient to be determined at the end of a year, after first-line treatment with a tyrosine kinase inhibitor, notably imatinib, particularly imatinib mesylate:

if the score S is less than 1, the patient treated with imatinib mesylate will have around at least a 40% chance of having, a year after the start of treatment with said imatinib mesylate, a major molecular remission, whereas if the score S is more than or equal to 1, the prognosis will be worse and the patient treated with imatinib mesylate will have less than around a 40% chance of having, one year after the start of treatment with said imatinib mesylate, a major molecular remission.

In this invention, a "major molecular response means the disappearance or virtual disappearance of cells expressing BCR-ABL transcripts, and advantageously an unrecombined BCR-ABL/ABL ratio of less than or equal to 0.1%. As the purpose of the treatment given to the patient is a complete remission of the disease, it is clearly preferable that the BCR-ABL transcript will no longer be detectable at all. However, it is currently considered that the above-mentioned unrecombined BCR-ABL/ABL ratio of less than or equal to 0.1% is generally speaking broadly satisfactory. This complies with European recommendations for monitoring patients suffering from chronic myeloid leukemia, as published in Baccarani et al. 2013, Blood, 122(6), 872-884. These recommendations can be summarized as follows:

- if the rate of BCR-ABL/ABL transcript measured by quantitative PCR is less than or equal to 10% after three months of treatment, less than or equal to 1% after six months of treatment and less than or equal to 0.1% after twelve months of treatment with a tyrosine kinase inhibitor, the treatment will be optimal,
- whereas, if the rate of BCR-ABL/ABL transcript measured by quantitative PCR is more than 10% after six months of treatment and more than 1% after twelve months of treatment with a tyrosine kinase inhibitor, it is recommended that the treatment be changed.

If the unrecombined BCR-ABL/ABL ratio is within 0.1 and 10, it will therefore represent an "intermediate molecular response." Lastly, if the unrecombined BCR-ABL/ABLE ratio is greater than 10, it will represent a "poor responder" or a "non-responder."

In the invention, the genes for which the expression level is measured are shown by their messenger RNA, obtained during the transcription of said genes, or their complementary DNA. Clearly, the transcription of genes is a process well known in the state of the art so no explanation thereof is needed.

Some genes whose expression level is measured within the scope of the invention are capable of expressing several variants, i.e. several molecules of messenger RNA that differ in their sequence. These variants are generally achieved by alternative splicing, said splicing allowing one or more parts of the expression product of said gene to be added, removed or modified. Here, too, there is no need to explain the splicing mechanism, which is well known in the state of the art.

The following genes are central to the method according to the invention:
- the CAT gene represented by the sequence SEQ ID NO: 1, encoding catalase,
- the SOD1 gene represented by the sequence SEQ ID NO: 2, encoding Superoxide dismutase [Cu—Zn],
- the GPX1 gene, represented by the sequence SEQ ID NO: 3, and in particular its variant 1, GPX1(1), encoding Glutathione peroxidase 1,
- the GPX4 (1-2-3) gene, represented by the sequence SEQ ID NO: 4, and in particular its variants 1 to 3, encoding Glutathione peroxidase 4,
- the PDRX1 gene, represented by the sequence SEQ ID NO: 5, and in particular its variants 1 to 3, encoding Peroxyredoxin,
- the SOD2 (1-2-3) gene, represented by the sequence SEQ ID NO: 6, encoding for Superoxide dismutase 2, and
- the GPX2 gene, represented by the sequence SEQ ID NO: 7, encoding Glutathione peroxidase 2.

Furthermore, as stated above, due to the presence of variants for certain genes, it is possible in order to measure the expression:
- of gene GPX4(1-2-3) to measure the expression of the nucleic acids comprising or being formed by sequences SEQ ID NO: 4 and/or SEQ ID NO: 8 and/or SEQ ID NO: 9,
- of gene PRDX1 to measure the expression of the nucleic acids comprising or being formed by sequences SEQ ID NO: 5 and/or SEQ ID NO: 10 and/or SEQ ID NO: 11, and
- of gene SOD2(1-2-3) to measure the expression of the nucleic acids comprising or being formed by sequences SEQ ID NO: 6 and/or SEQ ID NO: 12 and/or SEQ ID NO: 13.

The table below summarizes the advantageous genes according to the invention.

| Name of gene | SEQ ID NO | Name of gene | SEQ ID NO |
|---|---|---|---|
| CAT | SEQ ID NO: 1 | PRDX1 | SEQ ID NO: 5 |
| SOD1 | SEQ ID NO: 2 | | SEQ ID NO: 28 |
| GPX1 | SEQ ID NO: 3 | | SEQ ID NO: 29 |
| GPX4(1-2-3) | SEQ ID NO: 4 | SOD2(1-2-3) | SEQ ID NO: 6 |
| | SEQ ID NO: 26 | | SEQ ID NO: 30 |
| | SEQ ID NO: 27 | | SEQ ID NO: 31 |
| | | GPX2 | SEQID NO: 7 |

The sequences indicated above correspond to the complementary DNA sequences corresponding to the genes indicated.

The molecular tools used in the invention to measure the expression of the genes having variants are such that they enable the expression level of all of the variants of the same gene to be measured simultaneously.

Furthermore, within the scope of the invention, when the expression level of gene GPX4(1-2-3) represented by the sequence SEQ ID NO: 1 is measured, in fact the expression of the variants of said gene are being simultaneously measured, i.e. the expression level of the nucleic acid molecules of sequence SEQ ID NO: 4, SEQ ID NO: 8 and SEQ ID NO: 9 are being simultaneously measured.

In order to overcome the variabilities linked to experiments, the expression level of each of the genes of interest of the invention, i.e. at least the genes of sequence SEQ ID NOS: 1 to 7, and their variants when they exist, chosen from the genes of sequence SEQ ID NOS: 1 to 25, is standardized in relation to the expression level of one or more genes whose expression level is not modulated (increased or reduced) in the context of chronic myeloid leukemia, or more generally in the context of any disease.

The gene or genes enabling standardization are commonly called "housekeeping genes," which correspond to genes encoding proteins participating in the architecture of the cells, such as actin or tubulin, or even genes encoding enzymes of the metabolism, such as for example the gene GAPDH encoding glyceraldehyde-3-phosphate dehydrogenase.

Thus, in practice, for a given gene, its expression level is measured and a value 1 is obtained. In parallel, the expression level of GAPDH is measured and a score of 2 is obtained.

The standardized expression level of said given gene, if it is used for example in the northern blot technique, is then obtained by the following ratio: score1/score2.

As mentioned previously, the expression level of the genes studied in the above-mention prognosis method is compared with the expression level of the same genes taken from biological samples taken from healthy individuals. The expression level of the genes taken from said healthy biological samples is also standardized in relation to one or more "housekeeping" genes.

Furthermore, the ratio i as defined in Formula 1 can be redefined as follows:

$$\text{Ratio } i = \frac{\frac{\text{score1 } i \text{ (patient)}}{\text{score2 (patient)}}}{\frac{\text{score1 } i(\text{sain})}{\text{score2 (sain)}}}$$

[Key: sain = healthy]

where
- score1 i (patient) is the expression level measured for gene i in the sample taken from the patient,
- score2 (patient) is the expression level measured for the housekeeping gene in the sample taken from the patient,
- score1 i (healthy) is the expression level measured for gene i in the sample taken from a healthy individual,
- score2 (healthy) is the expression level measured for the housekeeping gene in the sample taken from a healthy individual.

Thus, Formula 1 can be rewritten as follows:

$$S = \sum \frac{\frac{\text{score1 } i \text{ (patient)}}{\text{score2 (patient)}}}{\frac{\text{score1 } i(\text{sain})}{\text{score2 (sain)}}} - \sum \frac{\frac{\text{score1 } j \text{ (patient)}}{\text{score2 (patient)}}}{\frac{\text{score1 } j(\text{sain})}{\text{score2 (sain)}}}$$

[Key: sain = healthy]

where i and j are integers, i varying from 1 to 5 and j varying from 6 to 7. Another formula would be as follows:

$$S = \left( \frac{\frac{\text{score1 1 (patient)}}{\text{score2 (patient)}}}{\frac{\text{score1 1(sain)}}{\text{score2 (sain)}}} + \frac{\frac{\text{score1 2 (patient)}}{\text{score2 (patient)}}}{\frac{\text{score1 2(sain)}}{\text{score2 (sain)}}} + \frac{\frac{\text{score1 3 (patient)}}{\text{score2 (patient)}}}{\frac{\text{score1 3(sain)}}{\text{score2 (sain)}}} + \frac{\frac{\text{score1 4 (patient)}}{\text{score2 (patient)}}}{\frac{\text{score1 4(sain)}}{\text{score2 (sain)}}} + \frac{\frac{\text{score1 5 (patient)}}{\text{score2 (patient)}}}{\frac{\text{score1 5(sain)}}{\text{score2 (sain)}}} \right) - \left( \frac{\frac{\text{score1 6 (patient)}}{\text{score2 (patient)}}}{\frac{\text{score1 6(sain)}}{\text{score2 (sain)}}} + \frac{\frac{\text{score1 7 (patient)}}{\text{score2 (patient)}}}{\frac{\text{score1 7(sain)}}{\text{score2 (sain)}}} \right)$$

[Key: sain = healthy]

In the particular case of using a quantitative method for measuring gene expression, and in particular by quantitative PCR, for each gene two independent samples will be used, and the ratio will be calculated by $2^{-\Delta\Delta Ct}$ where $\Delta\Delta Ct = \Delta Ct\text{sample1} - \Delta Ct\text{sample2}$ and $\Delta Ct = Ct$ RNA−reference Ct RNA (see below).

Another formula with therefore be as follows:

$$S = \sum 2^{-\Delta\Delta Ct\, i} - \sum 2^{-\Delta\Delta Ct\, j}$$

where i varies from 1 to 5 and j varies from 6 to 7, i.e.

$$S = (2^{-\Delta\Delta Ct1} + 2^{-\Delta\Delta Ct2} + 2^{-\Delta\Delta Ct3} + 2^{-\Delta\Delta Ct4} + 2^{-\Delta\Delta Ct5}) - (2^{-\Delta\Delta Ct6} + 2^{-\Delta\Delta Ct7}).$$

In an advantageous embodiment, the invention concerns an in vitro prognosis method as defined above, wherein
if S is greater than or equal to 1 and less than or equal to 2, said individual will have from a 40% to a 10% chance of having a major molecular remission one year after the start of treatment with a first-generation tyrosine kinase inhibitor.

Advantageously, it is possible to refine the prognosis of the patient and determine what his major molecular response will be one year after treatment with a first-generation tyrosine kinase inhibitor, in particular imatinib mesylate.

Thus, if:
the score S is less than 1, said individual will have at least around a 40% chance after 1 year of having a major molecular remission if he is treated with a first-generation tyrosine kinase inhibitor,
the score S is greater than 1 but less than or equal to 2, said individual will have a 40% to a 10% chance after 1 year of having a major molecular remission if he is treated with a first-generation tyrosine kinase inhibitor.

This means that the higher the score S, the greater the patient's risk of developing a resistance to the first-generation tyrosine kinase inhibitor, or, in other words, the smaller the chances after 1 year of having a major molecular remission.

More advantageously, the invention concerns a method of in vitro prognosis as defined above, wherein:
if S is greater than 2, said individual will have less than a 10% chance of having a major molecular remission one year after starting treatment with a first-generation tyrosine kinase inhibitor.

In other words, according to this advantageous embodiment, the invention concerns an in vitro prognosis method as previously defined, wherein, if:
the score S is less than 1, said individual will have at least around a 40% chance after 1 year of having a major molecular remission if he is treated with a first-generation tyrosine kinase inhibitor,
the score S is greater than 1 but less than or equal to 2, said individual will have a 40% to 10% chance after 1 year of having a major molecular remission if he is treated with a first-generation tyrosine kinase inhibitor, and
S is greater than 2, said individual will have less than a 10% chance after 1 year of having a major molecular remission if he is treated with a first-generation tyrosine kinase inhibitor.

Surprisingly, the inventor observed that the expression level of at least the 7 genes of sequence SEQ ID NOS: 1 to 7 varied depending on the prognosis of the patients treated with a first-generation tyrosine kinase inhibitor.

Thus, the invention can advantageously be defined as an in vitro method for the prognosis of the response to a treatment of an individual suffering from chronic myeloid leukemia, based on a leukemic biological sample taken from said individual, said method comprising:
a. a step of measuring the expression level of the genes from at least one subgroup of genes chosen from a group of genes,
said group of genes consisting of 25 genes, said 25 genes comprising or being formed by the nucleic acid sequences SEQ ID NO: 1 to SEQ ID NO: 25, said subgroup consisting in 7 genes, said 7 genes comprising or being formed by the nucleic acid sequences SEQ ID NO: 1 to SEQ ID NO: 7,
a value of the expression level measured being obtained for each of the genes of said subgroup,
b. a step of comparing the value attributed to the preceding step with each of said genes of said subgroup to the value attributed to each of said genes of said subgroup obtained from a healthy biological sample, in order to obtain a ratio for each of said genes of said subgroup of the expression level in the leukemic biological sample to the expression level in the healthy sample, and
c. a step of determining a score S according to the following formula $$S = \Sigma ratio\ i - \Sigma ratio\ j$$

where ratio i and ratio j represent respectively the ratios obtained for said genes of said subgroup comprising or being formed by the nucleic acid sequences SEQ ID NO: i or SEQ ID NO: j,
where i and j are integers, i varying from 1 to 5 and j varying from 6 to 7, so that:
if the score S is less than 1, said individual will have at least around a 40% chance after 1 year of having a major molecular remission if he is treated with a first-generation tyrosine kinase inhibitor,
if the score S is greater than 1 but less than or equal to 2, said individual will have a 40% to 10% chance after 1 year of having a major molecular remission if he is treated with a first-generation tyrosine kinase inhibitor, and
if S is greater than 2, said individual will have less than a 10% chance after 1 year of having a major molecular remission if he is treated with a first-generation tyrosine kinase inhibitor.

Even more advantageously, the invention concerns the above-mentioned method wherein:
if the score S is less than 1, said individual will have
at least around a 40% chance after 1 year of having a major molecular remission if he is treated with a first-generation tyrosine kinase inhibitor, and
less than around a 60% chance after 1 year of having an intermediate molecular remission if he is treated with a first-generation tyrosine kinase inhibitor,
if the score S is greater than 1 but less than or equal to 2, said individual will have
up to a 40% chance after 1 year of having an intermediate molecular remission is he is treated with a first-generation tyrosine kinase inhibitor, and
up to around a 25% chance after 1 year of being a poor responder if he is treated with a first-generation tyrosine kinase inhibitor,
and
if S is greater than 2, said individual will have
less than a 10% chance after 1 year of having a major molecular remission if he is treated with a first-generation tyrosine kinase inhibitor,
up to around a 40% chance after 1 year of having an intermediate molecular remission if he is treated with a first-generation tyrosine kinase inhibitor, and
around a 50% chance or more of being a poor responder if he is treated with a first-generation tyrosine kinase inhibitor.

In the invention, an "intermediate molecular response" means the quantity of BCR-ABL transcripts in the intermediate-level cells, and advantageously an unrecombined BCR-ABL/ABL ratio of between 0.1% and 10% inclusive ([0.1%-10%]).

In the invention, a "poor responder" means a patient whose quantity of BCR-ABL transcripts in the cells is at an intermediate level, and advantageously with an unrecombined BCR-ABL/ABL ratio of more than 10%.

In another embodiment, the invention concerns a method for the in vitro prognosis as previously defined, wherein the value of the expression level measured is obtained by a measurement of the expression of said genes of the subgroup by using a quantitative measuring method, in particular the quantitative PCR method.

In order to measure the expression level of the genes of interest, different techniques known to a person skilled in the art can be used:

the northern blot is a molecular biology method enabling the analysis of RNA. It derives from the southern blot method except that instead of studying DNA, RNA is studied. The RNA is analyzed by electrophoresis, enabling the RNAs to be separated on the basis of their size. They are then detected by a DNA or RNA probe. The northern blot method enables the distribution of RNAs within the tissues to be assessed and their relative abundance to be studied. It is therefore possible to deduce from these observations the more or less important expression of certain genes. The use of radioactive or fluorescent markers enables the expression level to be quantified.

DNA chips: the principle of DNA chips, the use of which has spread since the 1990s, is related to the northern blot method because it is based on fixing isolated fragments of retro-transcribed DNA fragments onto a support and hybridizing with a probe made from DNA.

Quantitative PCR: The principal of quantitative PCR known as "real-time" PCR lies in the possibility of following the quantity of DNA present in the reaction at any moment and not at the end of the PCR (end-point PCR). Fluorescent probes fix either to the double-stranded DNA (SYBR technology) or to a precise DNA sequence (Taqman and Beacon technology). These probes only fluoresce when fixed to the DNA (either because of a "quencher" or because fluorescence requires a double-stranded DNA). A fluorescence threshold is established by the program of the real-time PCR machine. Once the quantity of DNA allows the fluorescent probes to exceed this threshold a PCR cycle number is obtained, called a "Ct," which stands for "Cycle Threshold." It is this value that forms the basis of the calculations to quantify DNA absolutely or relatively. It is important to know the efficiency E of the PCR. For this, a real-time PCR is performed on samples of increasing dilution in order to obtain a standard curve corresponding to the pair of primers used (specific to the locus of interest). For example, a 1/2 dilution series ($D_{n+1}=D_n/2$) must, in theory give offset amplification curves of a PCR cycle each time. If this is the case, the reaction then has an efficiency of 2 (the quantity of DNA doubles at each cycle). In practice, the program of the real-time PCR machine can calculate the efficiency E of the reaction. More often, a real-time PCR over a dilution series with a known initial quantity of DNA enables the efficiency of the reaction to be calculated. The Cts are plotted on a graph with a logarithmic scale and the linear regression equation passing through these points gives the efficiency (this is the slope).

For reasons of practicality and specificity, it would be advantageous in the scope of the invention to use quantitative PCR adopting Taqman and Beacon technology: the expression of a gene is followed by an amplification by a pair of specific primers and the presence of a quencher probe enabling the number of molecules to be quantified.

More advantageously, the invention concerns a method of in vitro prognosis as previously defined, in which the value of the measured expression level is obtained by a measurement of the expression of said genes of the subgroup implemented by using at least those oligonucleotides comprising or being formed by sequences SEQ ID: 32 to 45, in particular the oligonucleotides comprising or being formed by sequences SEQ ID: 32 to 45 and the following sequences: 5'-tggggaag-3', 5'-ctgctggg-3', 5'-tgctggag-3', 5'-ggtggtgg-3', 5'-caggagaa-3', 5'-ctgcccca-3' and 5'-ctggctgg-3'.

In the invention, it is advantageous to determine the expression level of said 7 genes of sequence SEQ ID NOS: 1 to 7, and the variants envisaged above, represented by sequences SEQ ID NOS: 26 to 31, with the following oligonucleotides:

| Gene | Sense Oligonucleotide | Antisense Oligonucleotide | Taqman ® Probe |
|---|---|---|---|
| CAT | 5'-cgcagttcggttctccac-3'<br>SEQ ID NO: 32 | 5'-gggtcccgaactgtgtca-3'<br>SEQ ID NO: 33 | 5'-tgctggag-3' |
| SOD | 5'-gcatcatcaatttcgagcag-3'<br>SEQ ID NO: 34 | 5'-caggccttcagtcagtcctt-3'<br>SEQ ID NO: 35 | 5'-tggggaag-3' |
| GPX1 | 5'-caaccagtttgggcatcag-3'<br>SEQ ID NO: 36 | 5'-gttcacctcgcacttctcg-3'<br>SEQ ID NO: 37 | 5'-ggtggtgg-3' |
| GPX4 (1-2-3) | 5'-tacggacccatggaggag-3'<br>SEQ ID NO: 38 | 5'-ccacacacttgtggagctagaa-3'<br>SEQ ID NO: 39 | 5'-ctgcccca-3' |
| PRDX1 | 5'-cactgacaaacatggggaagt-3'<br>SEQ ID NO: 40 | 5'-tttgctcttttggacatcagg-3'<br>SEQ ID NO: 41 | 5'-ctggctgg-3' |
| SOD2 (1-2-3) | 5'-tccactgcaaggaacaacag-3'<br>SEQ ID NO: 42 | '5-taagcgtgctcccacacat-3'<br>SEQ ID NO: 43 | 5'-ctgctggg-3' |
| GPS2 | 5'-gtccttggcttcccttgc-3'<br>SEQ ID NO: 44 | '5-tgttcaggatctcctcattctg-3'<br>SEQ ID NO: 45 | 5'-caggagaa-3' |

In other words, this advantageous embodiment relates to an in vitro prognosis method as defined above, wherein the value of the measured expression level is obtained by a measurement of the expression of said genes of the subgroup implemented by using at least the oligonucleotides comprising or being formed by sequences SEQ ID: 32 to 45, so that Oligonucleotides SEQ ID NOS: 32 and 33 enable the expression of the gene of sequence SEQ ID NO: 1 to be measured Oligonucleotides SEQ ID NOS: 34 and 35 enable the expression of the gene of sequence SEQ ID NO: 2 to be measured Oligonucleotides SEQ ID NOS: 36 and 37 enable the expression of the gene of sequence SEQ ID NO: 3 to be measured Oligonucleotides SEQ ID NOS: 38 and 39 enable the expression of the gene of sequence SEQ ID NO: 4 to be measured Oligonucleotides SEQ ID NOS: 40 and 41 enable the expression of the gene of sequence SEQ ID NO: 5 to be measured Oligonucleotides SEQ ID NOS: 42 and 43 enable the expression of the gene of sequence SEQ ID NO: 6 to be measured Oligonucleotides SEQ ID NOS: 44 and 45 enable the expression of the gene of sequence SEQ ID NO: 7 to be measured in particular wherein the value of the measured expression level is obtained by measuring the expression of said genes of the subgroup implemented by using at least the oligonucleotides comprising or formed by sequences SEQ ID: 32 to 45, so that Oligonucleotides SEQ ID NO: 32, SEQ ID NO: 33 and 5'-tggggaag-3' enable the expression of the gene of sequence SEQ ID NO: 1 to be measured Oligonucleotides SEQ ID NO: 34, SEQ ID NO: 35 and 5'-ctgctggg-3' enable the expression of the gene of sequence SEQ ID NO: 2 to be measured Oligonucleotides SEQ ID NO: 36, SEQ ID NO: 37 and 5'-tgctggag-3' enable the expression of the gene of sequence SEQ ID NO: 3 to be measured Oligonucleotides SEQ ID NO: 38, SEQ ID NO: 39 and 5'-ggtggtgg-3' enable the expression of the gene of sequence SEQ ID NO: 4 to be measured Oligonucleotides SEQ ID NO: 40, SEQ ID NO: 41 and 5'caggagaa-3' enable the expression of the gene of sequence SEQ ID NO: 5 to be measured Oligonucleotides SEQ ID NO: 42, SEQ ID NO: 43 and 5'-ctgcccca-3' enable the expression of the gene of sequence SEQ ID NO: 6 to be measured, and Oligonucleotides SEQ ID NO: 44, SEQ ID NO: 45 and 5'-ctggctgg-3' enable the expression of the gene of sequence SEQ ID NO: 7 to be measured.

It is also advantageous to normalize the expression of each of the above-mentioned genes with the expression of GAPDH by using the oligonucleotides of SEQ ID NOS: 46 and 47, and of sequence 5'-tggggaag-3'.

Advantageously, the invention concerns an in vitro prognosis method as previously described, where the value of the measured expression level is obtained by a measurement of the expression of said genes of the subgroup, said measurement using the following oligonucleotides:

oligonucleotides SEQ ID NOS: 32 and 33 to measure the expression of the gene comprising or being formed by the sequence of nucleic acids SEQ ID NO: 1, oligonucleotides SEQ ID NOS: 34 and 35 to measure the expression of the gene comprising or being formed by the sequence of nucleic acids SEQ ID NO: 2, oligonucleotides SEQ ID NOS: 36 and 37 to measure the expression of the gene comprising or being formed by the sequence of nucleic acids SEQ ID NO: 3, oligonucleotides SEQ ID NOS: 38 and 39 to measure the expression of the gene comprising or being formed by the sequence of nucleic acids SEQ ID NO: 4, oligonucleotides SEQ ID NOS: 40 and 41 to measure the expression of the gene comprising or being formed by the sequence of nucleic acids SEQ ID NO: 5, oligonucleotides SEQ ID NOS: 42 and 43 to measure the expression of the gene comprising or being formed by the sequence of nucleic acids SEQ ID NO: 6, and oligonucleotides SEQ ID NOS: 44 and 45 to measure the expression of the gene comprising or being formed by the sequence of nucleic acids SEQ ID NO: 7.

This invention also concerns an in vitro personalized or theranostic method of diagnosis of an individual suffering from chronic myeloid leukemia, comprising a. a step of measuring the expression level of the genes from at least one subgroup of genes chosen from a group of genes,
   said group of genes consisting of 25 genes, said 25 genes comprising or being formed by the nucleic acid sequences SEQ ID NO: 1 to SEQ ID NO: 25,
   said subgroup consisting in 7 genes, said 7 genes comprising or being formed by the nucleic acid sequences SEQ ID NO: 1 to SEQ ID NO: 7,
   a value of the measured expression level being obtained for each of the genes of said subgroup, b. a step of comparing the value attributed to the preceding step with each of said genes of said subgroup to the value attributed to each of said genes of said subgroup obtained from a healthy biological sample, in order to obtain a ratio for each of said genes of said subgroup of the expression level in the leukemic biological sample to the expression level in the healthy sample, and c. a step of determining a score S according to the following formula $$S = \Sigma \text{ratio } i - \Sigma \text{ratio } j$$

where ratio i and ratio j represent respectively the ratios obtained for said genes of said subgroup comprising or being formed by the nucleic acid sequences SEQ ID NO: i or SEQ ID NO: j, where i and j are integers, i varying from 1 to 5 and j varying from 6 to 7, so that:

if S is less than 1, the chronic myeloid leukemia of said individual is chronic myeloid leukemia likely to respond preferentially to a treatment comprising a first-generation tyrosine kinase inhibitor, and if S is greater than or equal to 2, the chronic myeloid leukemia of said individual is chronic myeloid leukemia likely to respond preferentially to a treatment comprising a first- or subsequent-generation tyrosine kinase inhibitor.

In this method of personalized diagnosis, namely in vitro, of the invention, it is possible to determine which type of treatment it will be advantageous to provide to a patient suffering from chronic myeloid leukemia in order to obtain a major molecular response.

The inventor made the surprising observation that on measuring the expression level of genes belonging to the group of genes represented by the nucleic acids of sequences SEQ ID NO: 1 to SEQ ID NO: 7, and on applying the above-mentioned Formula 1, it is possible to determine which will be the best treatment to offer the patient. Indeed, if S, as calculated as indicated previously, is less than or equal to 1, the patient will have more than a 40% chance of having a major molecular response 1 year after the start of treatment if he is treated with a first-generation tyrosine kinase inhibitor, particularly with imatinib mesylate. Treatment with imatinib mesylate is therefore recommended and appropriate for this patient, greater than or equal to 2, the patient will have less than a 10% chance of having a major molecular response 1 year after the start of treatment if he is treated with a first-generation tyrosine kinase inhibitor, particularly with imatinib mesylate. It will therefore be appropriate to offer this patient another treatment and, in particular, to offer him a treatment based on a second- or subsequent-generation tyrosine kinase inhibitor.

In the particular case where $1 < S < 2$, the physician is confronted with a choice between treatment with a first-generation and second- or subsequent-generation(s) inhibitor. In this situation, the physician will then take into account clinical information, co-morbidities linked to potential secondary effects and clinical-biological prognostic scores (Sokal Score, etc.).

Advantageously, the invention concerns a method such as that previously defined, wherein the first-generation tyrosine kinase inhibitor is imatinib or one of its salts.

Imatinib mesylate is a potent and selective ATP-competitive inhibitor due to its binding site on ABL, inhibiting the activity of tyrosine kinase. It is currently the first-line treatment. It is used at a dose of 400 mg/day by mouth. It usually enables hematologic responses to be obtained within one to three months.

In the absence of a complete hematologic response in 3 months, the treatment will be deemed to have failed. The rate of hematologic remission after 5 years exceeds 98% and the rate of complete cytogenetic remission after 5 years is over 87%.

Side effects are frequent but of moderate intensity: nausea, diarrhea, cramps, edema and skin rashes. They are exacerbated in elderly patients. However, they rarely lead to the treatment being stopped.

Due to the risk of neutropenia and thrombopenia, the hemogram must be regularly monitored every 2 weeks for the first 3 months.

There are so-called primary resistances and other secondary (acquired) resistances.

Primary resistances are defined as a non-response situation in the hematologic, cytogenic and molecular context after precise periods of treatment. These then involve proposing other alternative treatments or increasing the doses.

By contrast, secondary resistances are defined by a loss of the initial response or by transformation. Several resistance mechanisms have been identified: modification of the intracellular bioavailability of imatinib, overexpression of the MDR (multidrug resistance) gene, amplification of BCR-ABL, mutations of the ABL kinase domain (>50 different mutations) and independent BCR-ABL mechanisms. In these cases, an increased dose can sometimes be effective (600 or even 800 mg/d) or else switching to a so-called second- or subsequent-generation tyrosine kinase inhibitor (TKI).

In another advantageous embodiment, the invention relates to a method as defined above, wherein the second-generation tyrosine kinase inhibitor is dasatinib or nilotinib, or one of their salts.

Dasatinib (Sprycel®) is a so-called 2nd-generation TKI, having proved its effectiveness in patients who are intolerant or have resistance mechanisms by mutations acquired from Glivec®. It is used at a dose of 100 mg/d. In addition to blocking the BCR/ABL kinase activity, it inhibits other transduction pathways such as the Src family kinases. Unlike imatinib, dasatinib binds simultaneously to the ABL kinase domain in its active and inactive conformation, which explains its high efficiency. Most of the mutations of reduced sensitivity to imatinib are sensitive to dasatinib, except for a mutation of the ABL ATP site, associated with a complete resistance (Threonine-to-Isoleucine at codon 315, T3151).

More recently, this molecule has obtained marketing authorization for second-line use.

Among the undesirable effects, the most prevalent are fluid retention (pleural and pericardial effusion), hematologic toxicity and diarrhea. This molecule is therefore to be avoided in the event of a history of hypertension, heart disease or respiratory disease. Some cases of pulmonary arterial hypertension have been reported.

Nilotinib (Tasigna®) is, like dasatinib, a so-called 2nd-generation TKI, having proved its effectiveness in patients who are intolerant or have resistance mechanisms by mutations acquired from Glivec®. It is a more potent imatinib analog. It can also target other protein kinases such as c-Kit receptors. Like imatinib, nilotinib binds to the inactive conformation of kinase. Its recommended dose is 400 mg twice a day at 12-h intervals and not during meals. Food affects its bioavailability.

Nilotinib is well tolerated. The main undesirable effects are the increase in lipase, bilirubin, blood sugar, hypophosphatemia and cutaneous toxicity, as well as hematologic toxicity, less pronounced than with dasatinib. The use of nilotinib is to be avoided for patients with a history of pancreatitis or poorly controlled diabetes, as well as patients with arteriopathy.

Subsequent-generation tyrosine kinase inhibitors are in particular: bosutinib, ponatinib or compounds undergoing clinical development, such as bafetinib.

The invention also relates to a kit, or pack, comprising:
a. at least the oligonucleotides comprising or formed by sequences SEQ ID: 32 to 45, in particular the oligonucleotides comprising or formed by sequences SEQ ID: 32 to 45 as well as the oligonucleotides formed by the following sequences: 5'-tggggaag-3', 5'-ctgctggg-3', 5'-tgctggag-3', 5'-ggtggtgg-3', 5'-caggagaa-3', 5'-ctgcccca-3' and 5'-ctggctgg-3', and
b. the nucleic acids from one or more healthy biological samples, particularly the nucleic acids from one or more samples of polymorphonuclear cells or neutrophils of the peripheral blood from one or more non-leukemic individuals, in other words from one or more individuals not suffering from leukemia.

A healthy biological sample is as defined above.

Advantageously, the kit, or pack, comprises:
a. at least the oligonucleotides comprising or formed by sequences SEQ ID: 32 to 45, in particular the oligonucleotides comprising or formed by sequences SEQ ID: 32 to 45 as well as the oligonucleotides formed by the following sequences: 5'-tggggaag-3', 5'-ctgctggg-3', 5'-tgctggag-3', 5'-ggtggtgg-3', 5'-caggagaa-3', 5'-ctgcccca-3', 5'-ctggctgg-3', 5'-ctggctgg-3' and 5'-tggggaag-3', and
b. the nucleic acids from a healthy biological sample, particularly the nucleic acids from a sample of polymorphonuclear cells or neutrophils of the peripheral blood from a non-leukemic individual.

The nucleic acids of the healthy sample are advantageously RNAs preserved in conditions limiting their degradation.

The pack or kit can also contain instructions on an appropriate support enabling the above-mentioned diagnostic or theranostic method to be implemented. This support may comprise, for example, instructions defining the quantitative PCR program (number of cycles, temperatures, etc.), and also a computer program product on an appropriate support enabling the calculation of S to be made, with the help of the above-mentioned formula.

Another aspect of the invention relates to software or a computer program product designed to implement the above-mentioned method and/or comprising portions/means/instructions of program code for executing said method when said program is executed on a computer. Advantageously, said program is provided on a data-recording support that can be read by a computer. Such a support is not limited to a portable recording support such as a CD-ROM but can also form part of a device comprising an internal memory of a computer (for example RAMs and/or ROMs), or of a device with external memory such as hard disks or USB sticks, or a proximity or remote server.

Advantageously, the invention concerns the above-mentioned computer program product, to implement steps b and c of the above-defined prognosis method.

A better understanding of the invention will emerge from the following four figures and example.

The genes are as follows: #1: SOD2, #2: GLRX1(1-2), #3: GSR, #4: PRDX5(1-3), #5: PRDX3(1-3), #6: TXN, #7: CAT, #8: SOD1, #9: GPX1(1), #10: GPX4(1-2-3), #11: PRDX2(1), #12: PRDX1(1-2-3), #13: GPX1(2), #14: GPX3, #15: GPX7, #16: TXN2, #17: PRDX5(2), #18: GLRX2(2), #19: GLRX5, #20: PRDX2(3), #21: PRDX4, #22: GLRX3, #23: PRDX6, #24: GPX2 and #25: GLRX2 (1).

Figure 2:
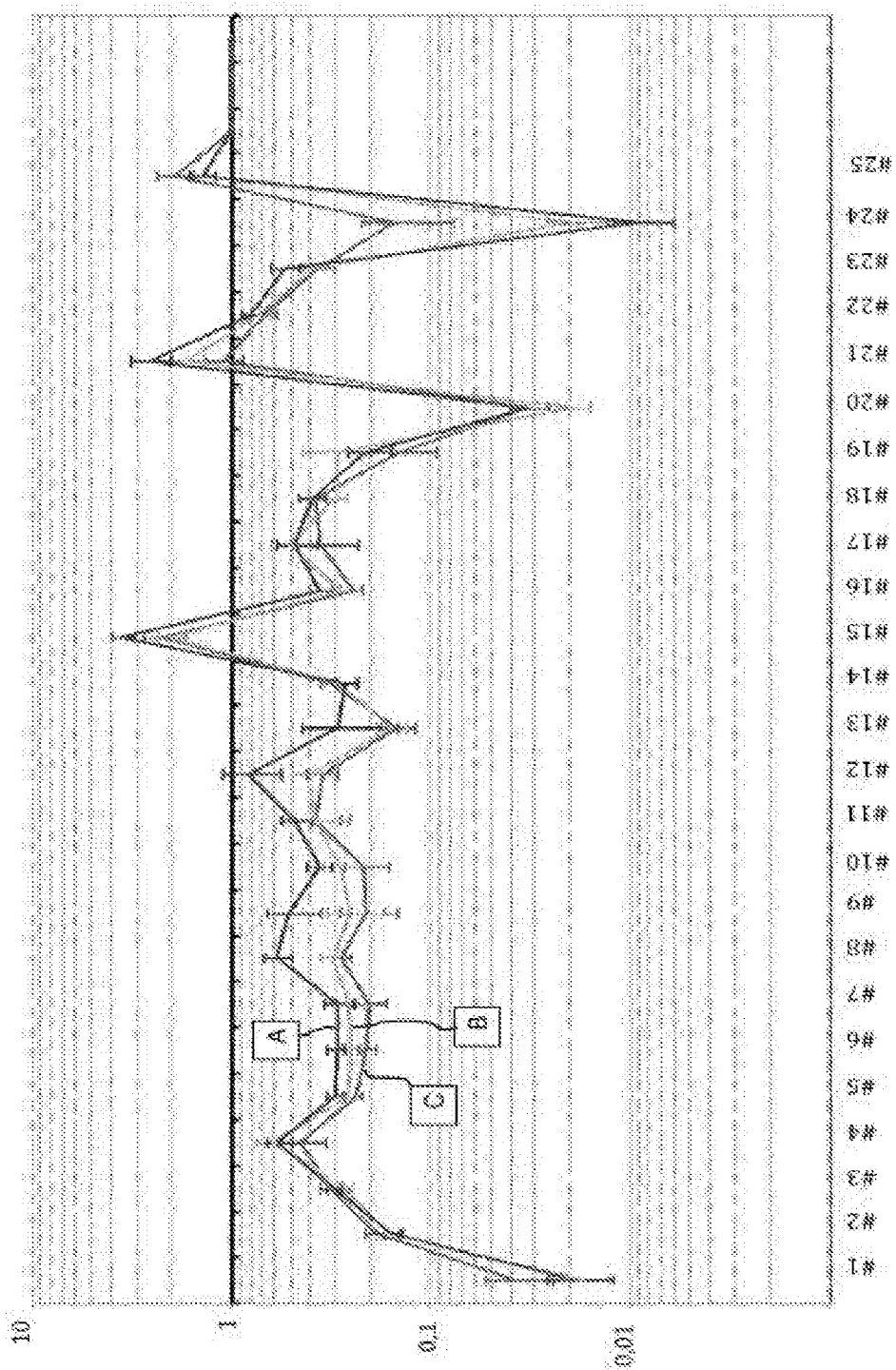

FIG. 2 represents a graph showing the expression level of the 25 genes tested in the 35 patients, and grouped according to their molecular response: A: major molecular response, B: intermediate molecular response and C: poor responders.

Figure 3:
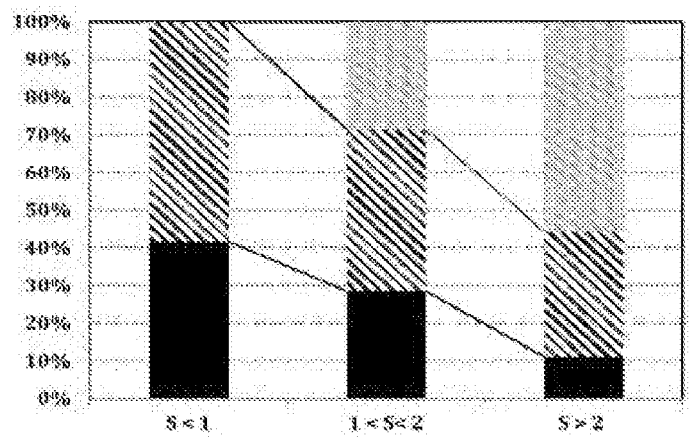

FIG. 3 is a histogram showing the distribution in percentage terms of the types of molecular responses depending on the calculated score S. The black regions correspond to a major molecular response, the hatched regions correspond to an intermediate molecular response and the grey regions correspond to poor responders.

Figure 4:
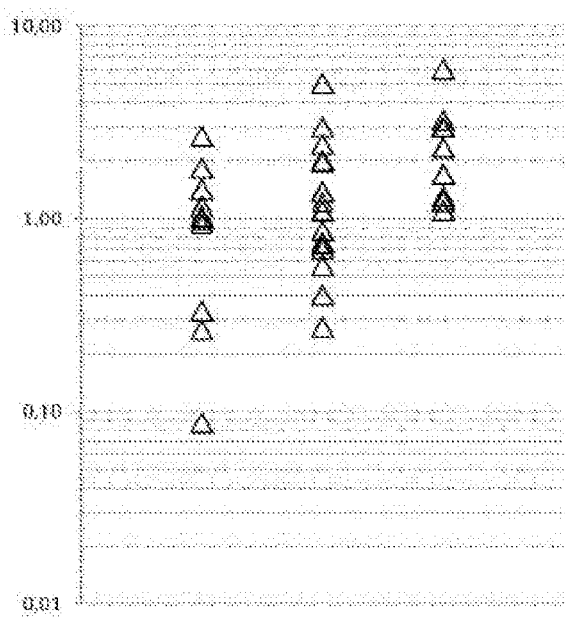

FIG. 4 is a graph showing the values of the score S (y-axis) based on the distribution of patients according to the molecular response to imatinib mesylate obtained one year after diagnosis (in the x-axis from left to right: major, intermediate or non-responder).

EXAMPLE

Material and Methods

1—Isolation of Polymorphonuclear Blood Cells

The polymorphonuclear cells of peripheral blood were isolated by centrifugation on Ficoll with a density of d=1.077.

2. Extraction of RNAs

The RNAs were extracted from $5.10^6$ cells. The latter were washed twice in PBS, followed by the addition of 1 mL of Trizol® (Invitrogen). The tubes were agitated (Vortex®) for 15 min to thoroughly lyse the cells. 200 µL of chloroform were added to obtain 3 phases, following 45 sec in the Vortex tube by tube and 15 min centrifugation at 12,000 rpm at 4° C. The top aqueous phase contained the RNAs, the intermediate phase contained the proteins and the bottom phase corresponded to chloroform and phenol. A second chloroform extraction was performed on the top phase containing the RNAs. Then 500 µL of isopropanol were added to the top phase of the second chloroform extraction. The tubes had to be returned about ten times for the isopropanol to precipitate the RNAs, then the latter were centrifuged for 10 min at 12,000 rpm. A first wash of the RNAs was performed in the bottom of the tube, to which was added 1 mL of 75% ethanol after centrifugation for 5 min at 7,500 rpm. A second wash was performed with 500 µL of 75% ethanol. The supernatant was eliminated once again by inversion and the tubes were upended on the pad for at least 20 min to allow all of the ethanol to evaporate. The RNA was then dissolved in 40 mL of DEPC water and the tubes were left for 1 h at −20° C. to allow the RNAs to dissolve properly.

3. RNA Assay and Analysis of their Purity and Quality

The RNA concentration was assessed by reading absorbance at 260 nm with the aid of a NanoDrop® spectrophotometer. RNA contamination was determined by comparing absorbance at 260 nm to that at 280 nm. The RNA was deemed to be free of contamination when the ratio of A260/A280 was between 1.9 and 2.1. RNA quality was then checked by a Bioanalyzer in accordance with the manufacturer's recommendations.

4. Reverse Transcription (RT)

Reverse Transcription (RT) is the synthesis reaction of a strand of DNA with a strand of DNA as a matrix. Reverse transcriptase is an RNA-dependent DNA polymerase synthesizing a so-called complementary DNA strand (cDNA) of an RNA strand. Moreover, this enzyme can only synthesize cDNA from a double strand zone created by the hybridization of RNA with a primer.

RT was performed using a SuperScript® VILO™ cDNA synthesis kit (Invitrogen). A reaction was carried out with a 5-µg tube of RNA previously aliquoted. Incubation of the tubes for 10 min at 70° C. allowed the RNA to be linearized for a better synthesis of cDNA. 50 µL of the following reaction mix were then added to each tube: 20 µL of DEPC water, 20 µL of 5× VILO buffer containing random primers, $MgCl_2$, dNTPs and a buffer optimized for RT, 10 µL of SuperScript® Enzyme Mix 10× containing SuperScript® III RT (RNA-dependent DNA polymerase reducing the activity of RNase H) and an RNaseOUT™ Recombinant Ribonuclease Inhibitor. The tubes were incubated for 10 min at ambient temperature then for 1 to 3 h at 42° C., which is the optimum temperature for Supercript® III RT to synthesize cDNA. The strands of matrix RNA were destroyed by incubating the tubes for 5 min at 85° C.

In order to check the quality of RT, a control PCR was performed for the encoding gene for β-actin, present in all non-muscle cells. The following reaction mix was prepared for a reaction: 35.6 µL of DEPC water (Invitrogen), 5 µL of 10× buffer (Roche), 1 µL of dNTPs (Amersham Biosciences), 1 µL of forward primer, 1 µL of reverse primer (Invitrogen), 2 µL of $MgCl_2$ (Roche) and 0.4 µL of Taq (EuroBio). A reaction mix to which 4 µL of RT product were added. The PCR was performed on the BIO-RAD C1000™ Thermal Cycler in accordance with the following program: 95° C. for 3 min (94° C. for 3 sec, 60° C. for 30 sec, 72° C. for 30 sec), repeated 34 times, 72° C. for 2 min and then 12° C. Migration was performed on agarose gel impregnated with TBE and revelation was made under UV light.

5. Real-Time PCR

The real-time PCR was carried out over a small number of cycles and using a fluorochrome whose fluorescence was proportional to the quantity of DNA.

The type of fluorescence detected here came from probes. The use of probes linked to the DNA strand corresponding to the gene of interest allowed fluorescence curves to be obtained that were proportional to the quantity of DNA. In fact, a probe is composed of DNA complementary to the target gene and comprises at one end a fluorophore and at the other end a "quencher" of fluorophore extinguisher. When the primers fix specifically to the DNA strand and the Taq polymerase progresses along the DNA strand (where the probe is fixed), the fluorophore is released and emits its fluorescence. As the cycles progress, the fluorescence emitted will increase and will be proportional to the quantity of amplicons formed.

The probes have a sequence enabling detection of patterns of 8 to 9 nucleotides whose prevalence in the transcriptome allows optimum coverage of the genes. With this type of probe, the specificity of the PCR derives from the primers. The threshold cycle (Ct) corresponds to the cycle during which the fluorescence of the amplified DNA becomes significantly different from the background noise. This threshold enables all of the amplifications to be compared during the exponential phase. In order for this relation to exist, it is necessary for the amplification efficiency to be 100%, in other words, for the efficiency E of the system to be 1. In fact, if E is different from 1, the relation between Ct and the initial quantity NO of RNA is no longer linear and any quantification is therefore impossible. The efficiency E of a PCR can be defined by plotting a curve on which Ct is shown on the basis of the dilution of the pair of primers. According to the following equation, the slope of the line corresponds to $-1/(\log(1+E))$. Based on this equation, we can write $E=10-1/slope-1$. So, when the efficiency E of the PCR is 1, the slope of the line is equal to $-1/\log 2=3.32$. The pairs of primers must have efficiencies E of more than 0.85, the arbitrary threshold below which the PCR is no longer quantitative. Moreover, in order to compare the quantity of RNA present in the two different samples, another invariant RNA is required as a reference, i.e. whose amplification efficiency is close to the amplification efficiency of the RNA studied. These RNAs are retro-transcribed from so-called "housekeeping" genes, i.e. whose transcription does not vary, or only a little.

In order to compare the relative quantities of RNA of interest between two samples, the quantity of interest relative to the quantity of reference RNA must first be normalized. This measurement, called ΔCt corresponds to the following calculation:

ΔCt=Ct RNA−reference ct RNA.

Then ΔΔCt=ΔCtsample1−ΔCtsample2 is calculated in order to obtain the relative variation expressed by the number $2^{-\Delta\Delta Ct}$.

The real-time PCR step was performed using a Roche "LightCycler® 480 Probes Master" kit.

For a reaction, the following reaction mix was prepared: 1.4 µL of "PCR grade" water, 5 µL of 2× reaction premix (containing TaqMan DNA polymerase, $MgCl_2$, dNTPs), 0.25 µL of each primer of the gene to be quantified and 0.1 µL of UPL probe. The cDNA was diluted to 1/3 and a standard range thereof was created from 10-1 to 10-3 then also diluted to 1/3, in order to assess the efficiency of the real-time PCR. The reaction mix and cDNA were distributed in a 384-well plate by a Vaudaux-Eppendorf epMotion® automated pipetting system. 7 μL of reaction mix and 3 μL of DNA diluted to 1/3 were distributed for one reaction. The real-time PCR was carried out using a Roche LightCycler® 480 according to the following program: incubation at 95° C. for 5 min to avoid interactions between the primers and thus improve sensitivity, 45 cycles of PCR at 95° C. for 10 sec and 60° C. for 30 sec, finishing with cooling at 40° C. for 30 sec. The excitation wavelength of the probes was 465 nm and for detection 510 nm.

The results obtained using the LightCycler® 480 were analyzed using LightCycler® 480 Software.

The qRT-PCR was performed on 7 genes (isoforms): SOD1, SOD2, CAT, SOD1, GPX1(1), GPX4(1-2-3), PRDX1(1-2-3) with calculation of the ΔCt (vs. GAPDH). The calculation of ΔΔCt (ΔCt–ΔCtm) was made for each gene. The variation coefficient compared to the healthy controls was then determined: RQ=2exp(−ΔΔCt) for each gene. The patient's score S was calculated by using the RQs calculated for each gene, according to the following formula:

$$S = \Sigma RQ[CAT, SOD1, GPX1(1), GPX4(1-2-3), PRDX1(1-2-3)] - \Sigma RQ[SOD2, GPX2].$$

Oligonucleotides Used sequences if they exist) in several biological samples (which are blood samples from donors not suffering from leukemia, purified of polymorphonuclear neutrophils) by normalizing this expression level to that of GAPDH.

This measurement of the expression level has made it possible to establish a standard expression level in healthy cells, Secondly, the inventor made the same types of measurements of the expression levels on samples during the diagnosis of 35 patients suffering from chronic myeloid leukemia by the Biological Hematology Department of Tours University Hospital in France.

The expression levels of each of the 25 genes, for each of the 35 patients, were compared to the expression level of said 25 genes in the healthy samples.

Figure 1:
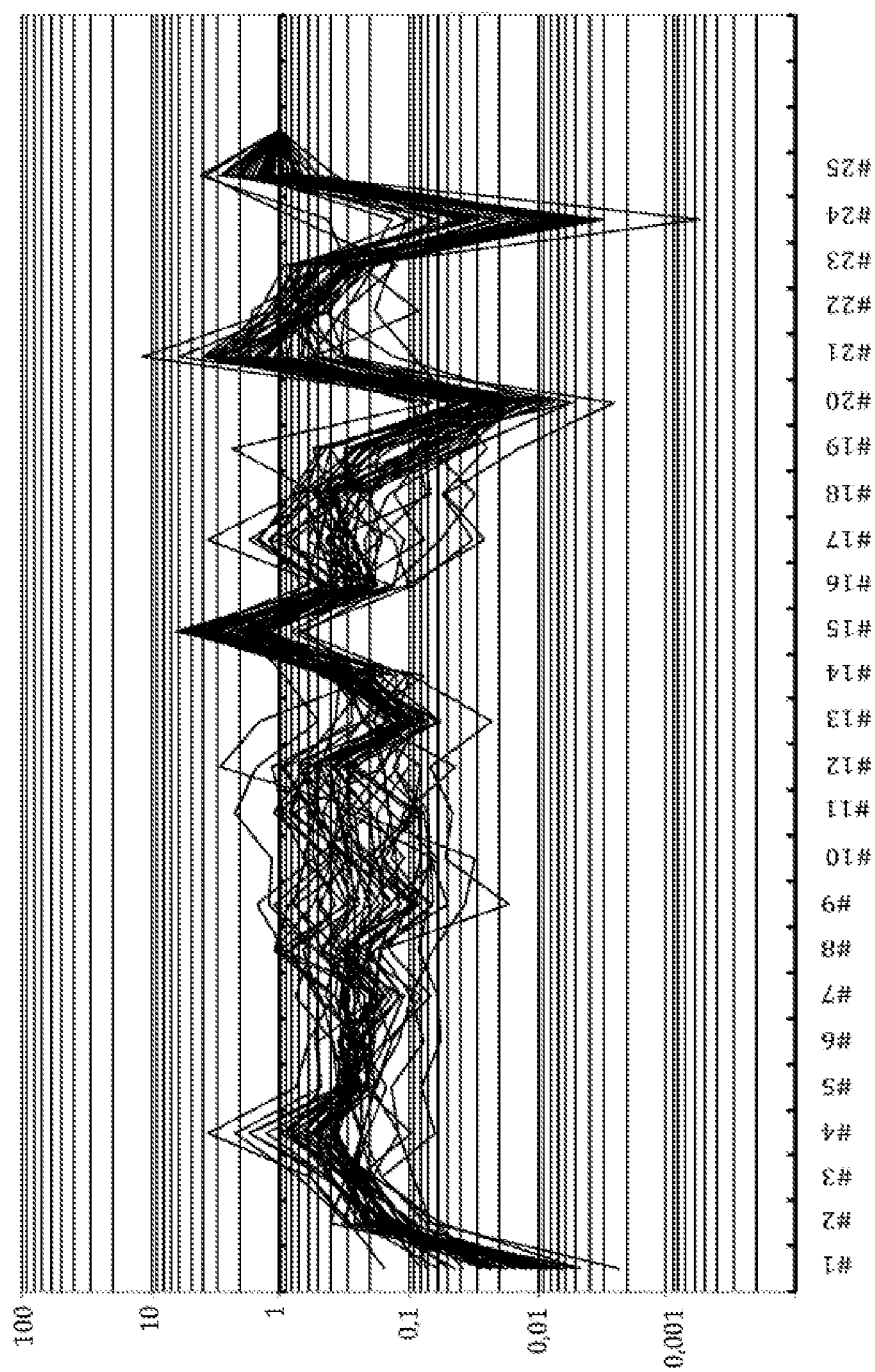
FIG. 1 represents a graph showing the expression level of the 25 genes tested in the 35 patients tested. The control level (corresponding to the expression of the genes in healthy samples) is normalized to 1. The scale is logarithmic.

FIG. 1 shows this comparison.

It will be observed in this figure that the expression of the 25 genes varies compared to the expression level measured in healthy samples, with for certain genes showing a wide variation between patients. This is the case particularly for genes SOD2: #1, CAT: #7, SOD1: #8, GPX1(1): #9, GPX4 (1-2-3): #10, PRDX1(1-2-3): #12 and GPX2: #24.

As the 35 patients were monitored regularly over the long term, the inventor was able to access their data, particularly their molecular response after one year of treatment with imatinib mesylate.

| Gene | Sense Oligonucleotide | Antisense Oligonucleotide | Probe |
|---|---|---|---|
| SOD1 | Gcatcatcaatttcgagcag<br>SEQ ID NO: 32 | Caggccttcagtcagtcctt<br>SEQ ID NO: 33 | tggggaag |
| SOD2 | Tccactgcaaggaacaacag<br>SEQ ID NO: 34 | Taagcgtgctcccacacat<br>SEQ ID NO: 35 | ctgctggg |
| CAT | Cgcagttcggttctccac<br>SEQ ID NO: 36 | Gggtcccgaactgtgtca<br>SEQ ID NO: 37 | tgctggag |
| GPX1_<br>var1 | Caaccagtttgggcatcag<br>SEQ ID NO: 38 | Gttcacctcgcacttctcg<br>SEQ ID NO: 39 | ggtggtgg |
| GPX2 | Gtccttggcttcccttgc<br>SEQ ID NO: 40 | Tgttcaggatctcctcattctg<br>SEQ ID NO: 41 | caggagaa |
| GPX4_<br>var1&2<br>&3 | Tacggacccatggaggag<br>SEQ ID NO: 42 | Ccacacacttgtggagctagaa<br>SEQ ID NO: 43 | ctgcccca |
| PRDX1_<br>var1&2<br>&3 | Cactgacaaacatggggaagt<br>SEQ ID NO: 44 | Tttgctcttttggacatcagg<br>SEQ ID NO: 45 | ctggctgg |
| GAPDH | Agccacatcgctcagacac<br>SEQ ID NO: 46 | Gcccaatacgaccaaatcc<br>SEQ ID NO: 47 | tggggaag |

Results

The inventor began with the starting hypothesis that the poor prognosis of a case of chronic myeloid leukemia would be linked to the frequency of leukemic stem cells. Leukemic stem cells have a reduced rate of reactive oxygen species (ROS). Furthermore, in order to maintain a low rate of ROS, leukemic stem cells should have a high metabolic activity of detoxification of ROS.

One way of increasing the ROS detoxification metabolism is to change the expression level of the genes encoding the enzymes involved in this process.

Firstly, the inventor measured by quantitative PCR the expression level of 25 genes encoding the main enzymes participating in ROS detoxification (and shown by sequences SEQ ID NOS: 1 to 25, or the variants of these Among the 35 patients, 10 had a major molecular response after 1 year, 16 had an intermediate molecular response and 9 were poor responders to said treatment.

By grouping the patients according to the above-mentioned response categories, the inventor was able to observe that the expression level of the above-mentioned 7 genes varied depending on the molecular response. The results are given in FIG. 2.

On this basis, the inventor proposed for each patient to add up the expression level values for genes whose expression was higher in the poor responders, and to subtract therefrom the expression level whose expression was lowest in the poor responders.

The inventor also proposed the formula:

$$S = \Sigma RQ[CAT, SOD1, GPX1(1), GPX4(1-2-3), PRDX1(1-2-3)] \Sigma RQ[SOD2, GPX2].$$

Retrospectively, with the data obtained from the samples of each patient taken during the diagnosis before treatment with imatinib mesylate, the inventor was able to calculate the score S.

The data are set out in the following tables:

Patients Having a Major Molecular Response after 1 Year

| patient | SOD2 | CAT | SOD1 | GPX1(1) | GPX4(1-2-3) | PRDX1(1-2-3) | GPX2 | Score S |
|---|---|---|---|---|---|---|---|---|
| 1 | 0.04 | 0.16 | 0.29 | 0.15 | 0.16 | 0.32 | 0.00 | 1.03 |
| 2 | 0.05 | 0.07 | 0.14 | 0.10 | 0.08 | 0.13 | 0.13 | 0.33 |
| 3 | 0.06 | 0.14 | 0.26 | 0.09 | 0.22 | 0.16 | 0.73 | 0.09 |
| 4 | 0.01 | 0.30 | 0.41 | 0.26 | 0.29 | 0.59 | 0.01 | 1.83 |
| 5 | 0.02 | 0.06 | 0.08 | 0.07 | 0.13 | 0.04 | 0.10 | 0.27 |
| 6 | 0.01 | 0.32 | 0.26 | 0.26 | 0.23 | 0.38 | 0.02 | 1.42 |
| 7 | 0.01 | 0.43 | 0.36 | 0.79 | 0.62 | 0.53 | 0.04 | 2.68 |
| 8 | 0.16 | 0.19 | 0.37 | 0.17 | 0.28 | 0.49 | 0.42 | 0.93 |
| 9 | 0.01 | 0.18 | 0.30 | 0.14 | 0.06 | 0.32 | 0.01 | 0.99 |
| 10 | 0.02 | 0.20 | 0.33 | 0.09 | 0.06 | 0.54 | 0.04 | 1.16 |

Patients Having an Intermediate Molecular Response after 1 Year

| patient | SOD2 | CAT | SOD1 | GPX1(1) | GPX4(1-2-3) | PRDX1(1-2-3) | GPX2 | score S |
|---|---|---|---|---|---|---|---|---|
| 11 | 0.01 | 0.29 | 0.24 | 0.09 | 0.23 | 0.26 | 0.00 | 1.10 |
| 12 | 0.00 | 0.10 | 0.17 | 0.02 | 0.05 | 0.07 | 0.00 | 0.40 |
| 13 | 0.02 | 0.08 | 0.25 | 0.22 | 0.18 | 0.38 | 0.00 | 1.09 |
| 14 | 0.01 | 0.29 | 0.48 | 0.29 | 0.35 | 0.63 | 0.03 | 2.01 |
| 15 | 0.02 | 0.34 | 0.18 | 0.05 | 0.07 | 0.13 | 0.01 | 0.74 |
| 16 | 0.01 | 0.24 | 0.21 | 0.10 | 0.16 | 0.10 | 0.06 | 0.75 |
| 17 | 0.01 | 0.49 | 0.85 | 0.31 | 0.66 | 0.69 | 0.01 | 2.98 |
| 18 | 0.01 | 0.15 | 0.34 | 0.10 | 0.30 | 0.34 | 0.00 | 1.21 |
| 19 | 0.01 | 0.74 | 0.57 | 1.20 | 1.15 | 1.49 | 0.09 | 5.06 |
| 20 | 0.08 | 0.12 | 0.22 | 0.08 | 0.16 | 0.08 | 0.00 | 0.57 |
| 21 | 0.01 | 0.35 | 0.29 | 0.48 | 0.36 | 0.98 | 0.02 | 2.43 |
| 22 | 0.01 | 0.09 | 0.07 | 0.04 | 0.03 | 0.12 | 0.06 | 0.27 |
| 23 | 0.02 | 0.11 | 0.45 | 0.75 | 0.24 | 0.44 | 0.00 | 1.97 |
| 24 | 0.02 | 0.19 | 0.16 | 0.06 | 0.20 | 0.28 | 0.00 | 0.87 |
| 25 | 0.00 | 0.37 | 0.33 | 0.13 | 0.27 | 0.29 | 0.00 | 1.38 |
| 26 | 0.04 | 0.18 | 0.17 | 0.12 | 0.12 | 0.16 | 0.01 | 0.70 |

Patients Who are Poor Responders after 1 Year

| patient | SOD2 | CAT | SOD1 | GPX1(1) | GPX4(1-2-3) | PRDX1(1-2-3) | GPX2 | Score S |
|---|---|---|---|---|---|---|---|---|
| 27 | 0.02 | 0.16 | 0.93 | 1.50 | 0.55 | 2.88 | 0.01 | 5.99 |
| 28 | 0.01 | 0.34 | 0.26 | 0.19 | 0.11 | 0.38 | 0.03 | 1.24 |
| 29 | 0.01 | 0.38 | 1.00 | 0.29 | 0.44 | 1.15 | 0.01 | 3.25 |
| 30 | 0.01 | 0.53 | 0.80 | 0.24 | 0.31 | 0.48 | 0.00 | 2.34 |
| 31 | 0.00 | 0.19 | 0.47 | 0.27 | 0.38 | 0.41 | 0.00 | 1.70 |
| 32 | 0.03 | 0.51 | 0.67 | 0.38 | 0.56 | 0.92 | 0.01 | 3.00 |
| 33 | 0.07 | 0.12 | 0.32 | 0.50 | 0.30 | 0.15 | 0.01 | 1.30 |
| 34 | 0.02 | 0.22 | 0.53 | 1.11 | 0.42 | 0.71 | 0.00 | 2.97 |
| 35 | 0.01 | 0.15 | 0.31 | 0.12 | 0.18 | 0.35 | 0.00 | 1.10 |

By reclassifying the patients according to their score S, the inventor surprisingly found that:

if S<1, around 40% of patients will have a major molecular response after 1 year, and around 60% of patients will have an intermediate response after 1 year. In other words, 100% of patients will have a molecular response, and none will be a poor responder, if 1≤S<2, around 30% of patients will have a major molecular response after 1 year, around 40% of patients will have an intermediate response after 1 year and notably around 30% of patients will be poor responders. In other words, around 70% of patients will have a molecular response, and if S>2, only 10% of patients will have a major molecular response, around 30% of patients will have an intermediate response, and more than 50% of patients will be poor responders. In other words, only around 40% of patients will respond to treatment with imatinib.

The results obtained for the 35 patients are set out in the following table:

| score | n = 10 RMM | n = 16 RMI | n = 26 R | n = 9 MR |
|---|---|---|---|---|
| S < 1 | 41.7% | 58.3% | 100.0% | 0.0% |
| 1 < S < 2 | 28.6% | 42.9% | 71.4% | 28.6% |
| S > 2 | 11.1% | 33.3% | 44.4% | 55.6% |

RMM: Major molecular response; RMI: Intermediate molecular response;

R: Response; MR: Poor responder.

FIG. 3 is a graphic representation of these results, showing the distribution of molecular responses after one year (black: major; hatched: intermediate; grey: non responder) depending on the score S.

FIG. 4 shows the distribution of patients according to their score S.

The invention is not limited to the embodiments presented and other embodiments will be obvious to a person skilled in the art.

The invention claimed is:

1. An in vitro method of prognosis for the response to a treatment of an individual suffering from chronic myeloid leukemia, based on a leukemic biological sample taken from said individual, said method comprising:
   a. measuring expression levels of at least each gene of a subgroup of genes from a group of genes,
      said group of genes consisting of 25 genes, said 25 genes consisting of nucleic acid sequences SEQ ID NO: 1 to SEQ ID NO: 25,
      said subgroup consisting of 7 genes, said 7 genes consisting of nucleic acid sequences SEQ ID NO: 1 to SEQ ID NO: 7,
   b. comparing the expressions levels of said genes to expression levels of each of said genes obtained from a healthy biological sample, and determining a ratio for each of said genes of the expression level in the leukemic biological sample to the expression level in the healthy sample, and
   c. determining a score S according to the following formula $S = \Sigma \text{ratio } i - \Sigma \text{ratio } j$ where ratio i and ratio j represent respectively the ratios obtained for said genes consisting of nucleic acid sequences SEQ ID NO: i or SEQ ID NO: j,
      where i and j are integers, i varying from 1 to 5 and j varying from 6 to 7, so that:
   if S is less than 1, said individual will have greater than 40% chance of having a major molecular remission one year after starting treatment with a first-generation tyrosine kinase inhibitor, and
   if S is greater than or equal to 1, said individual will have a less than 40% chance of having a major molecular remission one year after the start of treatment with a first-generation tyrosine kinase inhibitor.

2. The in vitro method of prognosis according to claim 1, wherein
   if S is greater than or equal to 1 and less than or equal to 2, said individual will have from a 40% to a 10% chance of having a major molecular remission one year after the start of treatment with a first-generation tyrosine kinase inhibitor.

3. The in vitro method of prognosis according to claim 1, wherein
   if S is greater than 2, said individual will have less than a 10% chance of having a major molecular remission one year after starting treatment with a first-generation tyrosine kinase inhibitor.

4. The in vitro method of prognosis according to claim 1, wherein the value of the expression level measured is obtained by a measurement of the expression of said genes of the subgroup by PCR.

5. The in vitro method of prognosis according to claim 1, wherein the value of the measured expression level is obtained by a measurement of the expression of said genes of the subgroup using an oligonucleotide selected from the group consisting of SEQ ID: 32 to 45.

6. The in vitro method of prognosis according to claim 1, wherein the value of the measured expression level is obtained by a measurement of the expression of said genes, said measurement using the following oligonucleotides:
   oligonucleotides SEQ ID NOS: 32 and 33 to measure the expression of the gene or consisting of the sequence of nucleic acids as set forth in SEQ ID NO: 1,
   oligonucleotides SEQ ID NOS: 34 and 35 to measure the expression of the gene consisting of the sequence of nucleic acids as set forth in SEQ ID NO: 2,
   oligonucleotides SEQ ID NOS: 36 and 37 to measure the expression of the gene consisting of the sequence of nucleic acids as set forth in SEQ ID NO: 3,
   oligonucleotides SEQ ID NOS: 38 and 39 to measure the expression of the gene consisting of the sequence of nucleic acids as set forth in SEQ ID NO: 4,
   oligonucleotides SEQ ID NOS: 40 and 41 to measure the expression of the gene consisting of the sequence of nucleic acids as set forth in SEQ ID NO: 5,
   oligonucleotides SEQ ID NOS: 42 and 43 to measure the expression of the gene consisting of the sequence of nucleic acids as set forth in SEQ ID NO: 6, and
   oligonucleotides SEQ ID NOS: 44 and 45 to measure the expression of the gene consisting of the sequence of nucleic acids as set forth in SEQ ID NO: 7.

7. An in vitro theranostic method of an individual suffering from chronic myeloid leukemia, comprising:
   a. measuring expression level of at least one gene of a subgroup of genes chosen from a group of genes,
      said group of genes consisting of 25 genes, said 25 genes consisting of nucleic acid sequences SEQ ID NO: 1 to SEQ ID NO: 25,
      said subgroup consisting in 7 genes, said 7 genes consisting of the nucleic acid sequences SEQ ID NO: 1 to SEQ ID NO: 7,
      a value of the expression level measured being obtained for each of said genes,
   b. a step of comparing the value attributed to the preceding step with each of said genes to the value attributed to each of said genes obtained from a healthy biological sample, in order to obtain a ratio for each of said genes of the expression level in the leukemic biological sample to the expression level in the healthy sample, and
   c. a step of determining a score S according to the following formula $S = \Sigma \text{ratio } i - \Sigma \text{ratio } j$ where ratio i and ratio j represent respectively the ratios obtained for said genes of said subgroup consisting of nucleic acid sequences SEQ ID NO: i or SEQ ID NO: j,
      where i and j are integers, i varying from 1 to 5 and j varying from 6 to 7, so that:
   if S is less than 1, the chronic myeloid leukemia of said individual is chronic myeloid leukemia likely to respond preferentially to a treatment comprising a first-generation tyrosine kinase inhibitor, and if S is greater than 2, the chronic myeloid leukemia of said individual is chronic myeloid leukemia likely to respond preferentially to a treatment comprising a second-generation tyrosine kinase inhibitor;

d. a step of administering to the individual:

a first-generation tyrosine kinase inhibitor if S is less than 1, or a second-generation tyrosine kinase inhibitor if S is greater than 2.

8. The method according to claim 7, wherein the first-generation tyrosine kinase inhibitor is imatinib or one of its salts.

9. The method according to claim 7, wherein the second-generation tyrosine kinase inhibitor is selected from the group consisting of dasatinib, nilotinib, and pharmaceutically acceptable salts thereof.

10. A computer program product on an appropriate support designed to implement solely steps b and c of the method of prognosis as defined in claim 1 and comprising portions or means or instructions of program code for executing said method of prognosis when said program is executed on a computer, wherein the support is selected from the group consisting of a portable recording support, an internal memory of the computer, a device with an external memory, a proximity server, and a remote server.

11. The method according to claim 7, wherein the first-generation tyrosine kinase inhibitor is imatinib and/or one of its salts.

12. A computer program product on an appropriate support designed to implement solely steps b and c of the theranostic method as defined in claim 7 and comprising portions or means or instructions of program code for executing said method of prognosis when said program is executed on a computer, wherein the support is selected from the group consisting of a portable recording support, an internal memory of the computer, a device with an external memory, a proximity server, and a remote server.

* * * * *

UNITED STATES PATENT AND TRADEMARK OFFICE
CERTIFICATE OF CORRECTION

PATENT NO.       : 10,961,588 B2
APPLICATION NO.  : 15/531242
DATED            : March 30, 2021
INVENTOR(S)      : Olivier Herault et al.

Page 1 of 1

It is certified that error appears in the above-identified patent and that said Letters Patent is hereby corrected as shown below:

On the Title Page

Item (73), Assignee, should read "Centre National De La Recherche Scientifique (CNRS), Paris, France; and Université De Tours, Tours Cedex 1, France."

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*